United States Patent [19]

Mihelich et al.

[11] Patent Number: 5,972,972
[45] Date of Patent: Oct. 26, 1999

[54] PYRAZOLES AS HUMAN NON-PANCREATIC SECRETORY PHOSPHOLIPASE $A_2$ INHIBITORS

[75] Inventors: Edward D. Mihelich, Carmel; Tulio Suarez, Greenwood; Gary A. Hite, Indianapolis, all of Ind.; Peter J. Doman; Stuart E. Willetts, both of Bossiney, United Kingdom

[73] Assignee: Eli Lilly and Company, Indianapolis, Ind.

[21] Appl. No.: 08/984,261

[22] Filed: Dec. 3, 1997

Related U.S. Application Data

[60] Provisional application No. 60/033,216, Dec. 4, 1996.
[51] Int. Cl.⁶ .......................... C07D 401/04; A61K 31/44
[52] U.S. Cl. .......................... 514/341; 514/404; 514/255; 514/307; 546/276.1; 546/144; 544/405; 548/368.7
[58] Field of Search .................. 546/276.1, 144; 514/341, 404, 255, 307; 548/368.7; 544/405

[56] References Cited

FOREIGN PATENT DOCUMENTS 539 034  4/1993  European Pat. Off. .

OTHER PUBLICATIONS

Chemical Abstracts, vol. 113: 24133 (1990), p. 682.
Chemical Abstracts, vol. 110: 104810 (1989), p. 650.
Chemical Abstracts, vol. 107: 187225 (1987).
Chemical Abstracts, vol. 107: 49477 (1987), p. 646.
Chemical Abstracts, vol. 64: 19628f (1966).
Chemical Abstracts, vol. 64: 19628e (1966).
Chemical Abstracts, vol. 63; 4012h (1965).
Chemical Abstracts, vol. 63: 4012g (1965).
Chemical Abstracts, vol. 60: 15879 (d).
Veldstra, et al., Recl. Trav. Chim. Paep Bas, 61 (1942), pp. 627–637.

*Primary Examiner*—Jane Fan
*Attorney, Agent, or Firm*—Arleen Palmberg

[57] ABSTRACT

A class of novel pyrazoles is disclosed together with the use of such compounds for inhibiting $sPLA_2$ mediated release of fatty acids for treatment of conditions such as septic shock.

10 Claims, No Drawings

PYRAZOLES AS HUMAN NON-PANCREATIC SECRETORY PHOSPHOLIPASE A$_2$ INHIBITORS

This applications claims the benefit of U.S. Provisional Application No. 60/033,216, filed Dec. 4, 1996.

This invention relates to novel substituted pyrazoles useful for inhibiting sPLA$_2$ mediated release of fatty acids for conditions such as septic shock.

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma-induced shock, bronchial asthma, allergic rhinitis, rheumatoid arthritis, etc.

It is desirable to develop new compounds and treatments for sPLA$_2$ mediated diseases.

This invention provides pyrazoles of the formula I

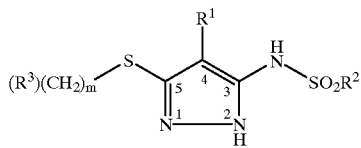

wherein:

R$^1$ is phenyl, isoquinolin-3-yl, pyrazinyl, pyridin-2-yl, pyridin-2-yl substituted at the 4-position with —(C$_1$–C$_4$)alkyl, (C$_1$–C$_4$)alkoxyl, —CN or —(CH$_2$)$_n$CONH$_2$ where n is 0–2;

R$^2$ is phenyl; phenyl substituted with 1 to 3 substituents selected from the group consisting of —(C$_1$–C$_4$)alkyl, —CN, halo, —NO$_2$, CO$_2$(C$_1$–C$_4$)alkyl and —CF$_3$; naphthyl; thiophene or thiophene substituted with 1 to 3 halo groups;

R$^3$ is hydrogen; phenyl; phenyl(C$_2$–C$_6$)alkenyl; pyridyl; naphthyl; quinolinyl; (C$_1$–C$_4$)alkyl thiazolyl; phenyl substituted with one or two substituents selected from the group consisting of— (C$_1$–C$_4$)alkyl, —CN, —CONH$_2$, —NO$_2$, —CF$_3$, halo, (C$_1$–C$_4$)alkoxy, CO$_2$(C$_1$–C$_4$)alkyl, phenoxy and SR$^4$ where R$^4$ is —(C$_1$–C$_4$) alkyl or halophenyl; phenyl substituted with one substituent selected from the group consisting of —O(CH$_2$)$_p$R$^5$ where p is 1 to 3 and R$^5$ is —CN, —CO$_2$H, —CONH$_2$, or tetrazolyl, phenyl and —OR$^6$ where R$^6$ is cyclopentyl, cyclohexenyl or phenyl substituted with halo or (C$_{1-C4}$) alkoxy; or phenyl substituted with two substituents which, when taken together with the phenyl ring to which they are attached form a methylenedioxy ring; and m is 1 to 5;

or a pharmaceutically acceptable salt, solvate, tautomer or prodrug derivative thereof.

These pyrazoles are effective in inhibiting human sPLA$_2$ mediated release of fatty acids.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula I.

According to a further aspect of the present invention, there is provided a method of selectively inhibiting sPLA$_2$ in a mammal in need of such treatment comprising administered to said mammal a therapeutically effective amount of a compound of formula I.

This invention also provides a method of alleviating the pathological effects of septic shock, adult respiratory distress syndrome, pancreatitis, trauma-induced shock, bronchial asthma, allergic rhinitis, rheumatoid arthritis, and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

Other objects, features and advantages of the present invention will become apparent from the subsequent description and the appended claims.

Definitions

As used herein, the term "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl and the like.

The term "halo" means chloro, fluoro, bromo or iodo.

The term, "alkenyl" employed alone or in combination with other terms means a straight chain or branched monovalent hydrocarbon group having the stated number range of carbon atoms and one double bond, typified by groups such as vinyl, propenyl, crotonyl, isopentenyl, and various butenyl isomers.

The term "phenyl(C$_2$–C$_6$ alkenyl)" refers to a straight or branched chain alkenyl group having from two to six carbon atoms attached to a phenyl ring which chain is attached to the remainder of the molecule. Typical phenylalkenyl groups include phenylethenyl, phenyl-2-propenyl, phenyl-2-butenyl, phenyl-3-butenyl, and phenyl-3-pentenyl.

The term "(C1–C4)alkyl thiazolyl " defines a thiazole substituted with a straight or branched chain alkyl group having from one to four carbon atoms attached to the remainder of the molecule at the thiazole ring. Typical (C1–C4)alkyl thiazolyl groups include methylthiazolyl, ethylthiazolyl, propylthiazolyl, isopropylthiazolyl, and butylthiazolyl.

The term "halophenyl" refers to a halo-substituted phenyl ring which ring is attached to the remainder of the molecule. Typical phenylhalo groups include fluorophenyl, chlorophenyl and bromophenyl.

The term "leaving group" means a substituent with an unshared electron pair that departs from the substrate in a nucleophilic substitution reaction. Preferred leaving groups include chlorine, bromine, tosylate and mesylate.

The salts of the above pyrazoles are an additional aspect of the invention. These salts can exist in conjunction with the acidic or basic portion of the molecule and can exist as acid addition, primary, secondary, tertiary or quaternary ammonium or alkali metal or alkaline earth metal salts. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprote, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, gylcollate, tartrate, methanesulfonate, propanesulfonate, naphthalene-1-sulfonate, naphthalene-2-sulfonate, mandelate and the like salts.

Where the compounds of the invention possess acidic functional groups various base addition salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable base addition salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.,* 66: 1–19 (1977)).

As is known in the art, pyrazole exists in two tautomeric structures, the first having the double bond at N1 and the proton on the N2 atom, referred to as a 2-H-pyrazole. The second tautomer has the proton at N1 and the double bond at N2 and is called a 1-H pyrazole. Since tetrazole tautomers are in constant equilibrium, the pyrazole structures in this invention are often referred to as 1(2)H-pyrazole and they may exist individually or as a combination of the two tautomers.

Prodrugs are derivatives of the compounds of the invention which have chemically or metabolically cleavable groups and become by solvoysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammlian organism (see, Bundgard, H., *Design of Prodrugs*, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Preferred esters include morpholinoethyloxy and diethylaminocarbonylmethoxy.

PREFERRED COMPOUNDS OF THE INVENTION

A preferred group of compounds of formula I are those where:

$R^1$ is pyridine-2-yl or pyridine-2-yl substituted at the 4-position with —$(C_1$–$C_4)$alkyl, $(C_1$–$C_4)$alkoxy, —CN or —$(CH_2)_n$CONH$_2$ where n is 0–2;

$R^2$ is phenyl substituted with 1 to 3 substituents selected from the group consisting of —$(C_1$–$C_4)$alkyl, —CN, halo, —NO$_2$, CO$_2(C_1$–$C_4)$alkyl and —CF$_3$; and $R^3$ is phenyl; phenyl$(C_2$–$C_6)$alkenyl; phenyl substituted with one or two substituents selected from the group consisting of —$(C_1$–$C_4)$alkyl, —CN, —CONH$_2$,—NO$_2$, —CF$_3$, halo, $(C_1$–$C_4)$alkoxy, CO$_2(C_1$–$C_4)$alkyl, phenoxy and SR$_4$ where $R^4$ is —$(C_1$–$C_4)$alkyl or halophenyl;

phenyl substituted with one substituent selected from the group consisting of —O(CH$_2$)pR$^5$ where p is 1 to 3 and $R^5$ is —CN, —CO$_2$H, —CONH$_2$ or tetrazolyl, phenyl and —OR$^6$ where $R^6$ is cyclopentyl, cyclohexenyl or phenyl substituted with halo or $(C_1$–$C_4)$alkoxy;

or phenyl substituted with two substituents which when taken together with the phenyl ring to which they are attached form a methylenedioxy ring.

Of this preferred group of compounds, somewhat more preferred compounds of formula I include compounds where $R^1$ is pyridin-2-yl substituted at the 4-position with (CH$_2)_n$ CONH$_2$ where n is 1; and $R^2$ is phenyl substituted with one or two substituents selected from the group consisting of —$(C_1$–$C_4)$alkyl and halo.

The most preferred compounds of the instant invention are 3-(2-chloro-6-methylphenylsulfonylamino)-4-(2-(4-acetamido)pyridyl)-5-(3-(4-fluorophenoxy)benzylthio)-(1H)-pyrazole and 3-(2,6-dichlorophenylsulfonylamino)-4-(2-(4-acetamido)pyridyl)-5-(3-(4-fluorophenoxy)benzylthio)-(1H)-pyrazole.

Preferred groups of compounds of formula I include the compounds with the following substituents:

(a) $R^1$ is phenyl, isoquinolin-3-yl or pyrazinyl;

(b) $R^1$ is pyridin-2-yl or pyridin-2-yl substituted at the 4-position with —$(C_1$–$C_4)$alkyl, $(C_1$–$C_4)$alkoxy, —CN or —$(CH_2)_n$CONH$_2$ where n is 1 to 2;

(c) $R^2$ is phenyl or phenyl substituted with 1 to three substituents selected from the group consisting of halo, NO$_2$, $(C_1$–$C_4)$alkyl, CO$_2(C_1$–$C_4)$alkyl, —CF$_3$ or —CN;

(d) $R^2$ is naphthyl, thiophene or thiophene substituted with 1 to 3 halo groups;

(e) $R^3$ is hydrogen;

(f) $R^3$ is pyridyl, naphthyl, quinolinyl or thiazole($C_1$–$C_4$) alkyl;

(g) $R^3$ is phenyl, phenyl$(C_2$–$C_6)$alkenyl, phenyl substituted with one or two substituents selected from the group consisting of (C$_1$–C$_4$)alkyl, —CN, —CONH$_2$, —NO$_2$, —CF$_3$, halo, (C$_1$–C$_4$)alkoxy, CO$_2$(C$_1$–C$_4$) alkyl, phenoxy or SR$^4$ where R$^4$ is —(C$_1$–C$_4$)alkyl or halophenyl;

(h) R$^3$ is phenyl substituted with —O(CH$_2$)$_p$R$^5$ where p is 1 to 3 and R$^5$ is hydrogen, —CN, —CO$_2$H, —CONH$_2$ or tetrazolyl;

(i) R$^3$ is phenyl substituted with OR$^6$ where R$^6$ is cyclopentyl, cyclohexenyl or phenyl substituted with halo or (C$_1$–C$_4$)alkoxy;

(j) R$^3$ is phenyl substituted with phenyl;

(k) R$^3$ is phenyl substituted with two substituents which when taken together with the phenyl ring to which they are attached form a methylenedioxy ring;

(1) m is 1 to 3.

Further typical examples of compounds of formula I which are useful in the present invention include.

3-(naphth-1-yl-4-sulfonylamino)-4-(pyridin-2-yl)-5-(2-pyridin-2-yl)ethylthio-(1H)-pyrazole;

3-(naphth-2-ylsulfonylamino)-4-(4-cyanopyridin-2-yl)-5-((4-quinolin-2-yl)but-1-yl)thio-(1H)-pyrazole;

3-(naphth-1-ylsulfonylamino)-4-((4-acetamido)pyridin-2-yl)-5-((5-carboxamidophenyl)pent-1-yl)thio-(2H)-pyrazole;

3-(naphth-2-ylsulfonylamino)-4-(4-methylpyridin-2-yl)-5-(3,5-dinitro)benzylthio-(1H)-pyrazole;

3-(naphth-1-ylsulfonylamino)-4-(pyridin-2-yl)-5-(4-methoxy)benzylthio-(1H)-pyrazole;

3-(naphth-2-ylsulfonylamino)-4-(pyridin-2-yl)-5-(3-(3-tetrazole-2-ylphenyl)prop-1-yl)thio-(1H)-pyrazole;

3-(naphth-1-ylsulfonylamino)-4-(4-t-butyl)pyridin-2-yl)-5-(2-(3-cyclopentyloxyphenyl)ethyl)thio-(2H)-pyrazole;

3-(naphth-2-ylsulfonylamino)-4-(pyrazin-2-yl)-5-(2-methylthiobenzyl)thio-(2H)-pyrazole;

3-(naphth-1-ylsulfonylamino)-4-(pyridin-2-yl)-5-((3-(4-phenoxy)phenyl)prop-1-yl)thio-(2H)-pyrazole;

3-(naphth-2-ylsulfonylamino)-4-phenyl-5-(2-(3-(4-fluorophenyl)phenyl)ethyl)thio-(1H)-pyrazole; 3-(3-nitro-5-ethyl)phenylsulfonylamino-4-(phenyl)-5-((3-cyanoprop-1-yloxy)benzyl)thio-(1H)-pyrazole;

3-(2-methylphenyl)sulfonylamino-4-(isoquinolin-3-yl)-5-(4-ethoxybenzyl)thio-(2H)-pyrazole;

3-(2,6-di(2-fluoroethyl)phenyl)sulfonylamino-4-(pyrazin-3-yl)-5-(cyclohexenyloxybenzyl)thio-(2H)-pyrazole;

3-(4-trifluoromethylphenyl)sulfonylamino-4-(isoquinolin-3-yl)-5-(3-phenyl-2-propen-1-yl)thio-(2H)-pyrazole;

3-(3,5-(di-t-butyl)phenyl)sulfonylamino-4-(pyrazin-2-yl)-5-((5-(naphth-1-yl)pent-1-yl)thio-(1H)-pyrazole;

3-(2-cyano-5-methoxycarbonylphenyl)sulfonylamino-4-(pyridin-2-yl)-5-(quinolin-2-yl)methylthio-(1H)-pyrazole;

3-(6-propoxycarbonyl)phenylsulfonylamino-4-(4-isopropylpyridin-2-yl)-5-(2-(3-methylthiazol-4-yl)ethyl)thio-(2H)-pyrazole;

3-(5-bromophenyl)sulfonylamino-4-(4-ethoxypyridin-2-yl)-5-(5-phenyl-2-hepten-1-yl)thio-(1H)-pyrazole;

3-phenylsulfonylamino-4-(4-cyanopyridin-2-yl)-5-(4-phenylbenzyl)thio-(1H)-pyrazole;

3-(3-methyl-5-methoxy)phenylsulfonylamino-4-(4-acetamidopyridin-2-yl)-5-(2-(2-propyl-6-cyanophenyl)ethyl)thio-(2H)-pyrazole;

3-(2,6-dinitrophenyl)sulfonylamino-4-phenyl-5-(4-carboxamidobenzyl)thio-(1H)-pyrazole;

3-(4-trifluoromethyl)phenylsulfonylamino-4-(isoquinolin-3-yl)-5-(4-(3-nitro-5-fluorophenyl)but-1-yl)thio-(1H)-pyrazole;

3-(2-cyano)phenylsulfonylamino-4-(pyrazin-2-yl)-5-(3,5-diethoxybenzyl)thio-(1H)-pyrazole;

3-(4-butoxyphenyl)sulfonylamino-4-(pyridin-2-yl)-5-(3-methoxycarbonylbenzyl)thio-(2H)-pyrazole;

3-(2-propoxycarbonylphenyl)sulfonylamino-4-(4-ethylpyridin-2-yl)-5-(3-(3-phenoxy-5-methoxycarbonylphenyl)prop-1-yl)thio-(1H)-pyrazole;

3-(3-nitrophenyl)sulfonylamino-4-(4-cyanopyridin-2-yl)-5-(3-methylthiobenzyl)thio-(1H)-pyrazole;

3-(3-methoxycarbonylphenyl)sulfonylamino-4-(4-carboxamidoethylpyridin-2-yl)-5-(4-(2-fluorophenylthio)benzylthio)-(2H)-pyrazole;

3-(4-chlorophenyl)sulfonylamino-4-(4-ethylpyridin-2-yl)-5-(2-cyano-5-ethylthiobenzyl)thio-(1H)-pyrazole;

3-phenylsulfonylamino-4-(4-methoxypyridin-2-yl)-5-(3-(3-carboxamidophenylthio)benzylthio)-(1H)-pyrazole;

3-(4-methoxycarbonylphenyl)sulfonylamino-4-(4-cyanopyridin-2-yl)-5-(4-cyanomethoxybenzyl)thio-(1H)-pyrazole;

3-(5-chlorophenyl)sulfonylamino-4-(4-carboxamidoethylpyridin-2-yl)-5-(3-carboxyethoxybenzyl)thio-(2H)-pyrazole;

3-(6-nitrophenyl)sulfonylamino-4-(phenyl)-5-(4-cyanomethoxybenzyl)thio-(1H)-pyrazole;

3-(2,6-dimethylphenyl)sulfonylamino-4-(isoquinolin-3-yl)-5-(4-(3-carboxamidoprop-1-yloxy)benzyl)thio-(1H)-pyrazole;

3-(3-methyl-5-methoxyphenyl)sulfonylamino-4-(pyrazin-2-yl)-5-(5-phenylethoxybenzyl)thio-(1H)-pyrazole;

3-(4-trifluoromethylphenyl)sulfonylamino-4-(pyridin-2-yl)-5-(3-(3-methoxyphenylmethoxy)benzyl)thio-(1H)-pyrazole;

3-(3-cyanophenyl)sulfonylamino-4-(4-t-butylpyridin-2-yl)-5-(3-(4-fluorophenylethoxy)benzyl)thio-(1H)-pyrazole;

3-(2-nitro-4-methylphenyl)sulfonylamino-4-(4-cyanopyridin-2-yl)-5-(2-quinolin-2-yl)ethylthio-(1H)-pyrazole;

3-(3,5-dichlorothiophene-2-yl)sulfonylamino-4-(4-methoxypyridin-2-yl)-5-(benzyl)thio-(1H)-pyrazole;

3-(thiophene-2-yl)sulfonylamino-4-(4-carboxamidomethylpyridin-2-yl)-5-(4-phenyl-3-buten-1-yl)thio-(2H)-pyrazole; 3-(4-bromothiophene-2-yl)sulfonylamino-4-(4-cyanopyridin-2-yl)-5-(pyridin-2-yl)methylthio-(2H)-pyrazole;

3-(5-fluorothiophene-2-yl)sulfonylamino-4-(4-carboxamidoethylpyridin-2-yl)-5-(2-naphth-1-yl)ethylthio-(2H)-pyrazole;

3-(2,6-difluorothiophene-2-yl)sulfonylamino-4-(isoquinolin-3-yl)-5-(2-ethylthiazole-4-yl)methylthio-(1H)-pyrazole;

3-(5-bromothiophene-2-yl)sulfonylamino-4-(pyrazin-3-yl)-5-(4-phenylbut-1-yl)thio-(1H)-pyrazole;

3-(3,5-difluorothiophene-2-yl)sulfonylamino-4-(4-ethylpyridin-2-yl)-5-(3,5-dimethylbenzyl)thio-(1H)-pyrazole;

3-(3,5-dichlorothiophene-2-yl)sulfonylamino-4-(4-cyanopyridin-2-yl)-5-(4-tetrazolylbenzyl)thio-(2H)-pyrazole;

3-(4-fluoro-3,5-dichlorothiophene-2-yl)sulfonylamino-4-(4-carboxamidoethylpyridin-2-yl)-5-(3-cyclohexen-3-yloxybenzyl)thio-(1H)-pyrazole;

3-(3-bromothiophene-2-yl)sulfonylamino-4-phenyl-5-(2-cyanomethoxybenzylthio)-(2H)-pyrazole;

3-(phenyl)sulfonylamino-4-(pyridin-2-yl)-5-(3-(2-tetrazolylethoxy)benzylthio)-(1H)-pyrazole;

Methods of Synthesis

Compounds of formula I can be prepared as described in Scheme I below.

Scheme I

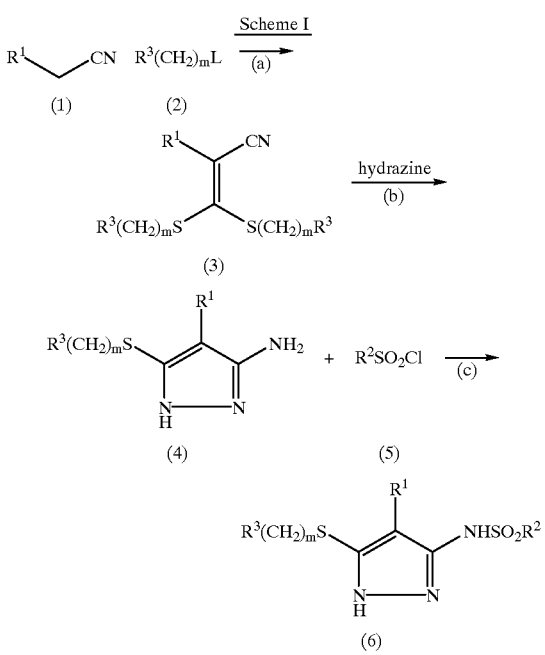

L is a leaving group.

In an aprotic polar solvent, such as tetrahydrofuran, an acetonitrile compound (1) is deprotonated by treatment with an excess of a strong base, such as sodium hydride, preferably under an inert gas, such as nitrogen. The deprotonated intermediate is treated with carbon disulfide and then alkylated twice with an appropriately substituted alkyl halide (2) of the formula $R^3(CH_2)_mL$, where L is a leaving group, preferably bromine, and $R^3$ and m are as defined above, to prepare intermediate compound (3). The reaction is conducted at ambient temperatures and is substantially complete in 1 to 24 hours.

Cyclization to form the amino substituted pyrazole (4) is achieved by reacting intermediate (3) with hydrazine at room temperature for from about 1 to 24 hours.

Selective sulfonylation of the amino group of intermediate (4) can be accomplished by treatment with a sulfonyl chloride (5) of the formula $R^2SO_2Cl$, where $R^2$ is as defined above, to prepare product (6). The reaction is preferably conducted in a solvent, such as pyridine, at ambient temperature for a period of time of from 1 to 24 hours. Preparation of 2,6-dimethylphenylsulfonyl chloride can be accomplished as described in J. Org. Chem. 25, 1996 (1960). All other sulfonyl chlorides are commercially available.

Preparation of Starting Materials

When $R^1$ is isoquinolinyl, pyrazinyl or pyridinyl substituted in the −4 position, starting material (1) of the formula $R^1CH_2CN$ can be prepared as described in Scheme II(a) below.

Scheme II(a)

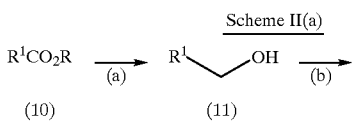

-continued

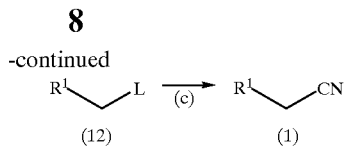

L is a leaving group

R is methyl or ethyl

An appropriately substituted ester (10) is reduced using an appropriate reducing agent, such as sodium borohydride with calcium chloride, as described in OPPI, 23, 204 (1991), to form the intermediate alcohol (11) which can be activated for displacement by converting to an appropriate leaving group such as a tosylate, mesylate or halogen.

The activated intermediate (12) may then be reacted with sodium cyanide or potassium cyanide in a polar aprotic solvent such as dimethyl formamide or dimethyl sulfoxide, displacing the leaving group and forming starting material (1) which can then be used to prepare the desired product as shown in Scheme I above.

Starting material (1) where R1 is pyridyl substituted at the 4-position with cyano or alkyl can be prepared according to Scheme II(b) below.

Scheme II(b)

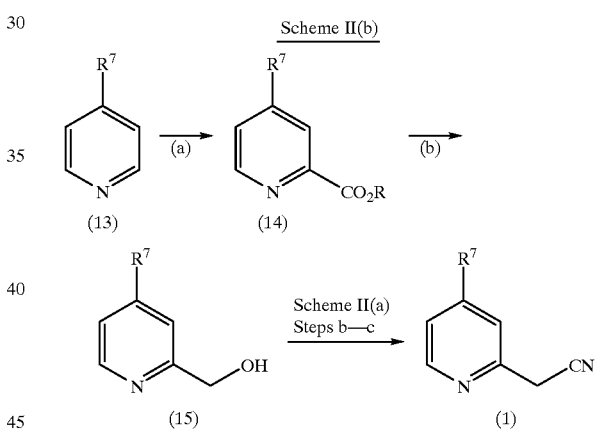

$R^7$ is —CN or —$(C_1-C_4)$alkyl.

R is methyl or ethyl.

Under Minisci reaction conditions, (Angew. Chem. Int. Ed., 24, 692(1985)), a 4-substituted pyridine (13) is converted to the ester (14) which may be readily reduced to intermediate (15) by employing an appropriate reducing agent, such as sodium borohydride with calcium chloride, as described in step (a), Scheme II(a).

Preparation of compounds where $R^1$ is pyridyl substituted with $(C_1-C_4)$alkoxy can be accomplished by converting 4-alkoxypyridine-N-oxide (16), under modified Minisci reaction conditions, to intermediate (17) as shown in Scheme II(c), below (Syn. Commun., 19, 317(1989)). Conversion to starting material (1) can then be easily accomplished using the process outlined in Scheme II(a), Steps (b–c).

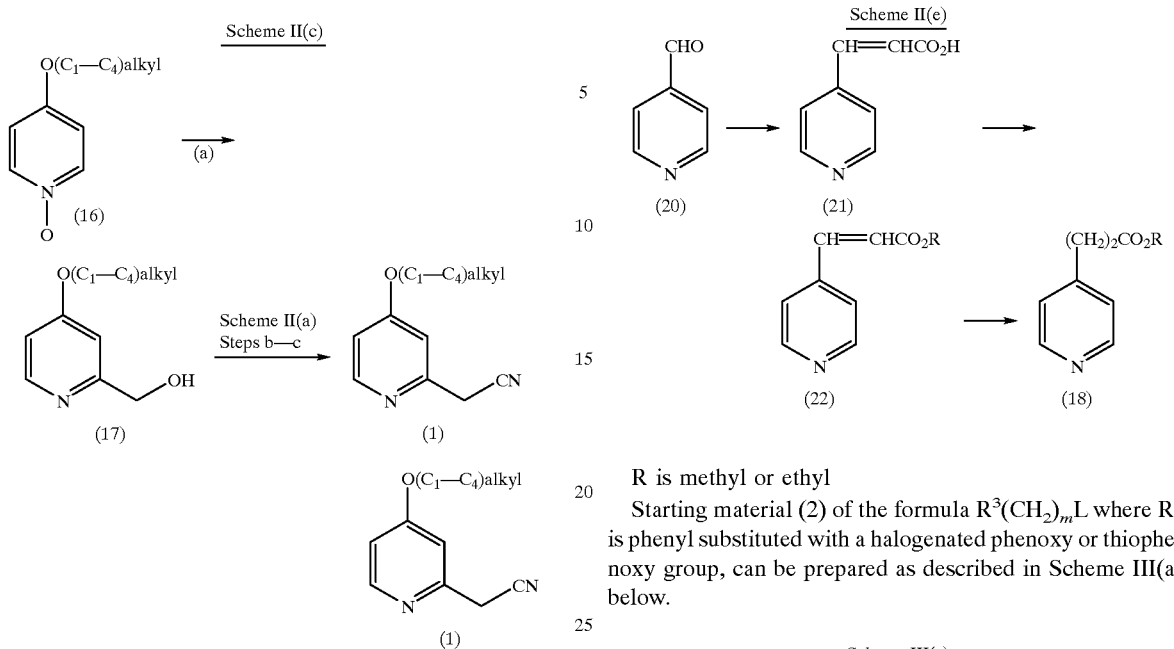

Compound (1) where $R^1$ is pyridyl substituted with $(CH_2)_n CONH_2$ are prepared as described in Scheme II(d) below.

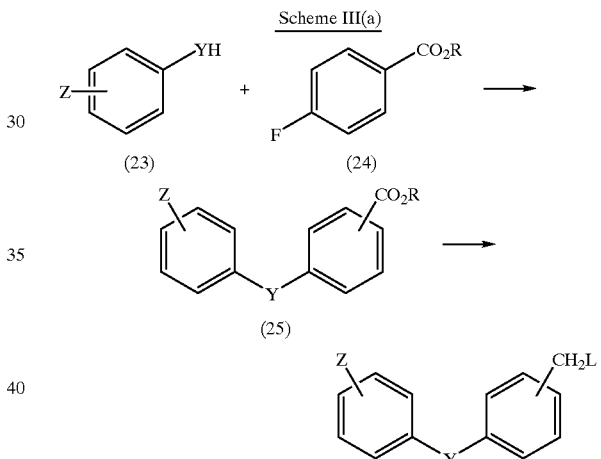

R is methyl or ethyl

Following the procedures outlined in Scheme II(a), Steps a, b, and c, the ester (18) is converted to the cyano/ester intermediate (19) which may then be converted to the amide (1) by treatment with concentrated ammonium hydroxide.

When n is 2, compound (18) is prepared as shown in II(e) below by condensing 4-pyridine carboxaldehyde (20) with malonic acid and a base, such as piperidine, to form cinnamic acid (21). Esterification of (21) under standard acidic conditions forms the ester (22). Hydrogenation can then be readily accomplished using a reducing agent, such as hydrogen and palladium on carbon to form (18).

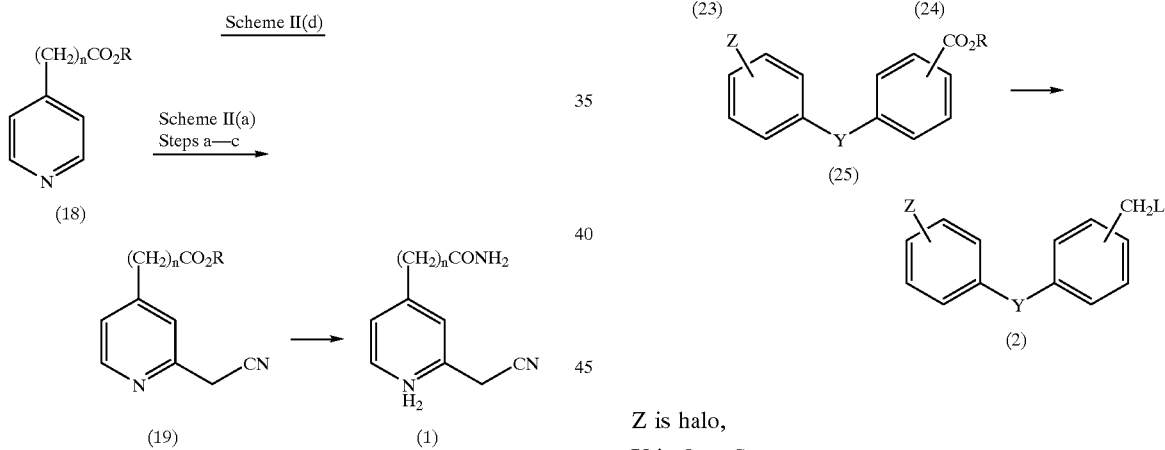

R is methyl or ethyl

Starting material (2) of the formula $R^3(CH_2)_m L$ where $R^3$ is phenyl substituted with a halogenated phenoxy or thiophenoxy group, can be prepared as described in Scheme III(a) below.

Z is halo,
Y is O or S,
R is methyl or ethyl
L is a leaving group

Using potassium fluoride and alumina, as described in J. Org. Chem., 58, 3229(1993), starting materials (23) and (24) are coupled to form intermediate (25). Reduction of the ester to the alcohol is achieved using lithium aluminum hydride, followed by conversion of the alcohol to a leaving group, such as a tosylate or mesylate group, or to a halogen by treatment, for example, with phosphorus tribromide, to form starting material (2).

Compound (2) where m is 1 and $R^3$ is phenyl substituted with $-O(CH_2)_p R^5$ where $R^5$ is $-CN$ can be prepared as outlined in Scheme III(b) below.

Scheme III(b)

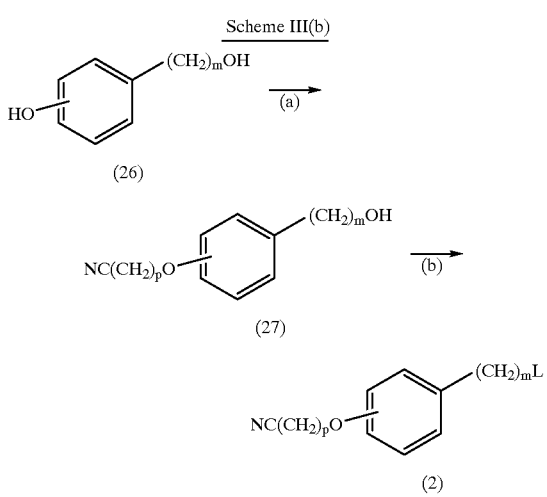

L is a leaving group.

Selective alkylation of (26) is achieved by treatment with a mild base, such as potassium carbonate and an alkylating agent of the formula $NC(CH_2)_pZ$, where Z is a halogen, to form (27). Conversion of the alcohol (27) to a leaving group is achieved, for example, by treatment with phosphorus tribromide to form compound (2) where L is bromine.

Conversion to the acetonitrile starting material (1) can be performed as described in Scheme II(a), Steps b–c.

When $R^3$ is phenyl substituted with a cyano group, conversion to the acid can be achieved by reacting the cyano product (6) with a base such as potassium hydroxide.

Conversion to the amide is accomplished by treatment of the cyano-substituted product (6) with postassium carbonate in the presence of hydrogen peroxide.

The tetrazole can be accomplished by refluxing the cyano-substituted product (6) with an excess of tributyl tin azide for from 1–24 hours followed by treatment with an acid such as hydrochloric acid.

Starting material (2) where $R^3$ is phenyl substituted with $CO_2(C_1-C_4)$alkyl can be prepared as illustrated below in Scheme III(c).

Scheme III(c)

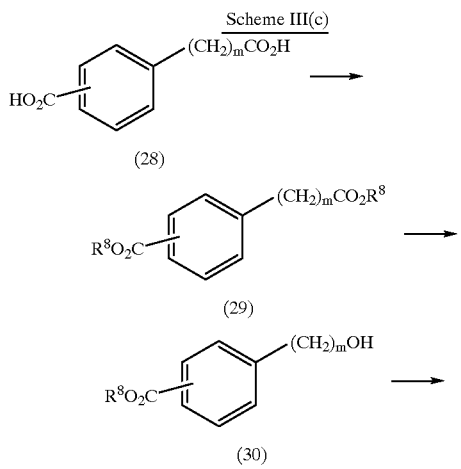

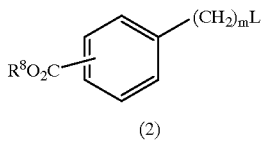

$R^8$ is $(C_1-C_4)$alkyl

L is a leaving group

Esterification of (28) using an acid, such as sulfuric acid, in a polar solvent, such as ethanol, prepares the diester (29). Selective reduction of the diester can be achieved by using a reducing agent, such as sodium borohydride (Synlett 419(1990)), in the presence of catalytic copper sulfate to form the alcohol (30) which is converted to a leaving group, preferably bromine, to form starting material (2) by treatment with carbonyl diimidazole and allylbromide. Chem. Pharm. Bull Japan 31, 4289 (1983) Additional compounds (2) of the formula $R^3(CH_2)_mL$ are either available from commercial sources or may be synthesized from commercially available alcohols via standard bromination reactions, such as phosphorus tribromide, carbon tetrabromide/triphenylphosphine or by reducing the corresponding commercially available aldehyde or carboxylic acid to the alcohol via standard reducing conditions such as sodium borohydride or lithium aluminum hydride and then converting to the bromide as described above.

Where m is 1 and $R_3$ is a meta-phenyl substituted phenyl group, a methyl group may be brominated under standard radical conditions using N-bromosuccinamide Starting materials of structure (2) where m is greater than 1 are available from commercial sources or compounds of this type may be readily prepared by chain extension methodology. For example, Friedman and Shani (L. Friedman and A. Shani J. Am. Chem. Soc. 1974, 96, 7102) demonstrate an effective method for chain extension of alkyl and aryl halides and summarize alternative methods as well.

The intermediates and final products may be isolated and purified by conventional techniques, for example by concentration of the solvents, followed by washing of the residue with water, then purification by conventional techniques, such as chromatography or recystallization.

It will be readily appreciated by the skilled artisan that the remaining starting materials are either commercially available or can be readily prepared by known techniques from commercially available starting materials. All other reactants used to prepare the compounds in the instant invention are commercially available.

The following examples further illustrate the preparation of the compounds of this invention. The example are illustrative only and are not intended to limit the socpe of the invention in any way.

The following abbreviations are used in Examples 1 to 13 below.

$Na_2SO_4$ is sodium sulfate
$MgSO_4$ is magnesium sulfate
$K_2CO_3$ is potassium carbonate
$CH_2Cl_2$ is methylene chloride
NaOH is sodium hydroxide
NH4Cl is ammonium chloride
THF is tetrahydrofuran
DMSO is dimethyl sulfoxide

EXAMPLE 1

3-(2,6-dichlorophenylsulfonylamino)-4-(2-pyridyl)-5-(3-(4-fluorophenoxy)benzylthio)-(1H)-pyrazole A. Preparation of 3,3-bis(3-(4-fluorophenoxy)benzylthio)-2-pyridylacrylonitrile 2-Pyridylacetonitrile (0.41 g, 3.50 mmol) in 10 ml of dry tetrahydrofuran (THF) was added dropwise to an ice-cooled slurry of 2.1 equivalents of sodium hydride (0.29 g of a 60% mineral oil dispersion) in 40 ml of dry THF under nitrogen. The resulting green slurry was stirred at room temperature for 30 minutes and then neat carbon disulfide (0.22 ml, 3.68 mmol) was added dropwise, resulting in an immediate precipitate choking the solution. More dry THF (10 ml) was added to aid stirring. After 15 minutes, commercial 3-(4-fluorophenoxy)benzyl bromide (2.0 g, 7.11 mmol) was added with 10 ml of dry THF. After stirring overnight at room temperature, the reaction mixture was poured into 100 ml of saturated $NH_4Cl$ solution and then extracted twice with 200 ml of diethylether. The organic extracts were washed with brine and then combined, dried over $MgSO_4$ and then concentrated to an oil. This oil was rinsed with pentane and then concentrated to afford 2.05 g of the subtitle compound pure enough for further use.

B. Preparation of 3-amino-4-(2-pyridyl)-5-(3-(4-fluorophenoxy)benzylthio)-(1H)-pyrazole 3,3-Bis(3-(4-fluorophenoxy)benzylthio)-2-pyridylacrylonitrile (2.03 g, 3.41 mmol), prepared as described above, was placed in 8 ml of hydrazine hydrate and stirred at room temperature overnight. The reaction was poured into 100 ml of water and was extracted twice with ethyl acetate (150 ml each). The organic extracts were washed with water and brine, combined, dried over $K_2CO_3$ and concentrated. Flash chromatography on silica with first chloroform and then a 3:1 chloroform/ethyl acetate mixture afforded 1.11 g (83% yield) of the subtitle compound.

$^1$H-NMR(300 MHz, $CDCl_3$): 8.52(d,1H); 8.12(d,1H); 7.62(t,1H); 7.21–6.73(m,11H); 5.75(br s,2H); 4.01(s,2H).

C. 3-(2,6-dichlorophenylsulfonylamino)-4-(2-pyridyl)-5-(3-(4-fluorophenoxy)benzylthio)-(1H)-pyrazole 3-Amino-4-(2-pyridyl)-5-(3-(4-fluorophenoxy) benzylthio)-(1H)-pyrazole (0.39 g, 0.99 mmol) was dissolved in 5 ml of pyridine. Commercial 2,6-dichlorobenzenesulfonyl chloride (0.26 g, 1.04 mmol) was added and the red solution was stirred overnight at room temperature. The reaction mixture was poured into 50 ml of water and was extracted twice with 100 ml portions of ethyl acetate. The organic layers were washed with water and brine, combined, dried over $MgSO_4$ and concentrated. The crude product was slurried in cold ethyl acetate and the solid was filtered off and washed with small portions of cold ethyl acetate and cold diethyl ether and dried under vacuum to afford 0.32 g (53% yield) of the final compound.

FD-MS: (M+)600 mp. 164–5° C.

Elemental analysis: Calc. C 53.91% H 3.18% N 9.31% S 10.66% Cl 11.79% Found C 54.19% H 3.20% N 9.37% S 9.80% Cl 11.79%

EXAMPLE 2

3-(2-chloro-6-methylphenylsulfonylamino)-4-(2-(4-acetamido)pyridyl)-5-(3-(4-fluorophenoxy) benzylthio)-(1H)-pyrazole A. Preparation of ethyl 4-(2-carboethoxy) pyridylacetate Ethyl pyruvate (84.4 g, 0.726 mol) was cooled in an ice/salt bath and treated dropwise with 30% hydrogen peroxide solution (55 g, 0.484 mol) keeping the temperature below 10° C. This solution was then added dropwise over 2 hours to an ice-cooled, vigorously stirred mixture of ethyl 4-pyridineacetate (8.00 g,0.0484 mmol), ferrous sulfate heptahydrate (134.6 g, 0.484 mol) and concentrated sulfuric acid (14.3 g, 0.145 mol) in 39 ml of water and 700 ml of dichloromethane ($CH_2Cl_2$). After stirring for an additional 15 minutes, the mixture was poured into 500 ml of cold water. The layers were separated and the aqueous layer was extracted with 400 ml of $CH_2Cl_2$. The separate organic phases were washed with 400 ml of a 5% sodium sulfite solution and then with 250 ml of brine. The organic layers were combined, dried over $Na_2SO_4$ and concentrated. Flash chromatography on silica using hexane and then 3:1 hexane/ethyl acetate afforded 7.12 g (62% yield) of the subtitle compound.

B. Preparation of ethyl 4-(2-hydroxymethyl) pyridylacetate

Ethyl 4-(2-carboethoxy)pyridylacetate (7.12 g, 30.0 mmol) was dissolved in 100 ml of absolute ethanol and cooled in an ice bath under nitrogen. Powdered anhydrous calcium chloride (1.82 g, 16.5 mmol) was added all at once. Sodium borohydride (0.63 g, 16.5 mmol) was then added in small portions over one hour. The reaction was stirred for 4 hours at 0° C. and then an additional 0.2 g of sodium borohydride was added. The reaction was stored overnight in the freezer at approximately –20° C. during which a solid precipitated. The solid was filtered off, washed with ethanol and discarded. The filtrate and washings were combined and evaporated to dryness. The residue was slurried in 50 ml of brine and extracted twice with 125 ml of chloroform. The organic extract was washed once with 40 ml of brine, dried over $Na_2SO_4$ and concentrated to afford 5.34 g (91% yield) of the subtitle compound.

C. Preparation of ethyl 4-(2-methanesulfonoxymethyl)pyridylacetate

Ethyl 4-(2-hydroxymethyl)pyridylacetate (3.34 g, 17.1 mmol) and triethylamine (2.86 ml, 20.5 mmol) were dissolved in 50 ml of dry dichloromethane ($CH_2Cl_2$) under nitrogen and cooled to –40° C. Methanesulfonyl chloride (1.46 ml, 18.8 mmol) was added dropwise in 10 ml of $CH_2Cl_2$ and the reaction was stirred for one hour and then allowed to warm to 0° C. The reaction mixture was then poured into ice cold water and extracted twice with $CH_2Cl_2$. The extracts were washed with brine, dried over $MgSO_4$ and concentrated to afford 4.42 g of the subtitle compound which was used immediately.

D. Preparation of ethyl 4-(2-cyanomethyl) pyridylacetate

Ethyl 4-(2-methanesulfonoxymethyl)pyridylacetate (4.42 g, 16.2 mmol) was added dropwise in 10 ml of dry dimethylsulfoxide (DMSO) to powdered sodium cyanide (2.50 g, 51.3 mmol) slurried in 15 ml of dry DMSO. The reaction was protected from light and stirred overnight at room temperature. The reaction mixture was poured into a cold solution of 70 g of $K_2CO_3$ in 210 ml of water and then extracted twice with 300 ml of diethyl ether. The extracts were washed with brine, dried over $Na_2SO_4$ and concentrated to afford 2.68 g (77% yield) of the subtitle compound.

E. Preparation of 4-(2-cyanomethyl) pyridylacetamide

Ethyl 4-(2-cyanomethyl)pyridylacetate (2.70 g, 13.2 mmol) was cooled in an ice bath and treated dropwise with 12 ml of ice-cold concentrated ammonium hydroxide. The reaction was stirred at room temperature for five hours and then evaporated to dryness. Flash chromatography on silica with first chloroform and then a 20:1 chloroform/methanol mixture afforded 1.96 g (84% yield) of the subtitle compound.

F. Preparation of 3,3-bis(3-(4-fluorophenoxy) benzylthio)-2-(4-acetamido)pyridylacrylonitrile 4-(2-Cyanomethyl)pyridylacetamide (0.36 g, 2.06 mmol) in 5 ml of dry tetrahydrofuran (THF) and 0.5 ml of dry dimethyl sulfoxide was added dropwise to an ice-cooled slurry of 2.1 equivalents of sodium hydride (0.17 g of a 60% mineral oil dispersion) in 12 ml of dry THF under nitrogen. The resulting slurry was stirred at room temperature for 2 hours and then neat carbon disulfide (0.14 ml, 2.26 mmol) was added dropwise. After 45 minutes, commercial 3-(4-fluorophenoxy)benzyl bromide (1.18 g, 4.21 mmol) was added with 5 ml of dry THF. After being stirred overnight at room temperature, the reaction mixture was poured into 50 ml of saturated $NH_4Cl$ solution and then extracted twice with 100 ml of diethyl ether. The organic extracts were washed with brine and then combined, dried over $MgSO_4$ and then concentrated to a solid. This solid was rinsed with pentane and then dried to afford 1.24 g of the subtitle compound pure enough for further use.

G. Preparation of 3-amino-4-(2-(4-acetamido) pyridyl)-5-(3-(4-fluorophenoxy)benzylthio)-(1H)-pyrazole 3,3-Bis(3-(4-fluorophenoxy)benzylthio)-2-(4-acetamido) pyridylacrylonitrile (1.24 g, 1.90 mmol) was dissolved in 30 ml of absolute ethanol and cooled in an ice bath. Ice-cold hydrazine hydrate (7 ml) was added slowly dropwise. The reaction was stirred at 0° C. for 8 hours and then stored at −20° C. for 60 hours. The reaction was diluted with 100 ml of ethyl acetate and then concentrated to dryness. The residue was slurried in brine and then extracted twice with 100 ml of ethyl acetate. The organic layers were washed with water and then brine, dried over $MgSO_4$ and concentrated. Flash chromatography on silica with chloroform and then a 20:1 chloroform/methanol mixture afforded 0.55 g (64% yield) of the subtitle compound.

H. Preparation of 3-(2-chloro-6-methylphenylsulfonylamino)-4-(2-(4-acetamidol) pyridyl)-5-(3-(4-fluorophenoxy)benzylthio)-(1H)-pyrazole By substantially following the procedures described for Example 1, Step C, the compound 3-(2-chloro-6-methylphenylsulfonylamino)-4-(2-(4-acetamidyl)pyridyl)-5-(3-(4-fluorophenoxy)benzylthio)-(1H)-pyrazole was afforded.

mp. 216–8° C.

Elemental analysis: Calc. C 56.47 H 3.95 N 10.97 Found C 56.17 H 4.00 N 10.81

EXAMPLE 3

3-(2,6-dichlorophenylsulfonylamino)-4-(2-(4-(3-propionamido))pyridyl)-5-(2-phenoxybenzylthio)-(1H)-pyrazole A. Preparation of 3-(4-pyridyl)acrylic acid 4-Pyridinecarboxaldehyde (18.96 g, 0.177 mol) and malonic acid (55.3 g, 0.53 mol) were placed in 200 ml of pyridine. Piperidine (5.25 ml, 0.053 mol) was added and the reaction was refluxed for 6 hours. The reaction mixture was cooled in an ice bath and then the white solid was filtered off and rinsed with ether and dried to afford 20.1 g of the subtitle compound. Concentration of the filtrate and then filtration and rinsing with ether resulted in recovery of another 2.2 g of product (84% total yield).

B. Preparation of ethyl 3-(4-pyridyl)acrylate 3-(4-Pyridyl)acrylic acid (16.18 g, 0.1085 mol) was slurried in 200 ml of absolute ethanol. Concentrated sulfuric acid (8 ml) was added and the reaction was refluxed for 3 hours. After cooling, the solvent was evaporated and the residue was cautiously neutralized with saturated sodium bicarbonate solution. The resulting mixture was then extracted twice with diethyl ether. The organic extracts were washed with water and then brine, dried over $MgSO_4$ and concentrated to afford 17.88 g (93% yield) of the subtitle compound.

mp. 64–5° C.

C. Preparation of ethyl 3-(4-pyridyl)propionate

Ethyl 3-(4-pyridyl)acrylate (16.62 g, 93.8 mmol) was hydrogenated in 80 ml of ethanol over 5% Pd on carbon (2 g) at 60 psi at room temperature for 16 hours. After evaporation, the residue was dissolved in 200 ml of diethyl ether and filtered through diatomaceous silica and concentrated to afford 15.97 g (95% yield) of the subtitle compound. D. Preparation of thyl 3-(4-(2-hydroxymethyl) pyridyl)propionate By substantially following the procedures described in Example 2 Step A and B, the subtitle compound is afforded.

E. Preparation of ethyl 3-(4-(2-chloromethyl) pyridyl)propionate hydrochloride

Ethyl 3-(4-(2-hydroxymethyl)pyridyl)propionate (2.76 g, 13.2 mmol) was dissolved in 5 ml of dry dichloromethane and cooled in an ice bath under nitrogen. Thionyl chloride (5 ml) was added slowly dropwise and the reaction was stirred several days at room temperature. After concentration, the residue was twice diluted with benzene and then evaporated to dryness to afford crude product (3.53 g) suitable for the next step.

F. Preparation of ethyl 3-(4-(2-cyanomethyl) pyridyl)propionate

Ethyl 3-(4-(2-chloromethyl)pyridyl)propionate hydrochloride (2.05 g, 7.76 mmol) in 5 ml of dry dimethylsulfoxide (DMSO) was added dropwise to a slurry of powdered sodium cyanide (1.52 g, 31.0 mmol) in 6 ml of dry DMSO. The reaction was protected from light and stirred at room temperature overnight. The reaction mixture was poured into a solution of 20 g of $K_2CO_3$ in 60 ml of water and then extracted twice with 150 ml of diethyl ether. The organic extracts were washed with water and then brine, dried over $Na_2SO_4$ and concentrated to afford 1.42 g (84% yield) of the subtitle compound.

G. Preparation of 3-(2,6-dichlorophenylsulfonylamino)-4-(2-(4-(3-propionamidol))pyridyl)-5-(2-phenoxybenzylthio)-(1H)-pyrazole By substantially following the procedures described for Example 2, Steps E, F and G and Example 1, Step C the compound 3-(2,6-dichlorophenylsulfonylamino)-4-(2-(4-(3- propionamido))pyridyl)-5-(2-phenoxybenzylthio)-(1H)-pyrazole was prepared.

mp. 178–80° C.

Elemental analysis: Calc. C 55.05 H 3.85 N 10.70 Found C 55.34 H 3.94 N 10.67

EXAMPLE 4

3-(2,6-dichlorophenylsulfonylamino)-4-(2-pyridyl)-5-(3-(4-carboethoxyphenyl)propylthio)-(1H)-pyrazole

A. Preparation of ethyl 3-(4-carboethoxyphenyl) propionate

The 3-(4-carboxyphenyl)propionic acid (21.0 g, 0.108 mol) was slurried in 200 ml of absolute ethanol. Concentrated sulfuric acid (8 g) was added and the reaction was refluxed overnight. After cooling, the solvent was evaporated and the residue was slurried in 50 ml of water. The resulting mixture was then extracted twice with diethyl ether. The organic extracts were washed twice with saturated sodium bicarbonate solution and then brine, dried over MgSO$_4$ and concentrated to afford 24.8 g (92% yield) of the subtitle compound.

B. Preparation of ethyl 3-(4-carboethoxyphenyl) propanol

The ethyl 3-(4-carboethoxyphenyl)propionate (1.23 g, 4.91 mmol) was dissolved in 11 ml of absolute ethanol, cooled in an ice bath, and treated with 0.25 ml of a 2 N cupric sulfate solution in water. Sodium borohydride (0.93 g, 24.6 mmol) was added in small portions over one hour. The reaction was stirred at room temperature over night and then evaporated. The residue was slurried in brine and extracted twice with chloroform. The extracts were filtered through celite, dried over MgSO$_4$, and concentrated to afford 1.0 g (98%) of the subtitle compound.

C. Preparation of ethyl 3-(4-carboethoxyphenyl) propyl bromide

The ethyl 3-(4-carboethoxyphenyl)propanol (1.00 g, 4.80 mmol) was dissolved in 8 ml of dry acetonitrile under nitrogen and treated with carbonyl diimidazole (1.01 g, 6.24 mmol). After ten minutes, allyl bromide (1.66 ml, 19.2 mmol) was added and the reaction was refluxed for 5 hours. After cooling, the mixture was evaporated, slurried in water and extracted twice with 5:1 pentane/diethyl ether solution. The organic extracts were washed with water and then brine, dried over MgSO$_4$ and concentrated to afford 1.15 g (88% yield) of the subtitle compound.

D. Preparation of 3-(2,6-dichlorophenylsulfonylamino)-4-(2-pyridyl)-5-(3-(4-carboethoxyphenyl)propylthio)-(1H)-pyrazole By substantially following the procedures described for Example 1, Steps A, B, and C the compound 3-(2,6-dichlorophenylsulfonylamino)-4-(2-pyridyl)-5-(3-(4-carboethoxyphenyl)propylthio)-(1H)-pyrazole was afforded.

mp.147–8° C.

Elemental analysis: Calc. C 52.79 H 4.09 N 9.47 Found C 52.61 H 4.07 N 9.42

EXAMPLE 5

3-(2,6-dichlorophenylsulfonylamino)-4-(2-pyridyl)-5-(4-(4-fluorophenoxy)benzylthio)-(1H)-pyrazole

A. Preparation of ethyl 4-(4-fluorophenoxy) benzoate p-Fluorophenol (1.66 g, 14.81 mmol) and ethyl p-fluorobenzoate (2.50 g, 14.87 mmol) were dissolved in 30 ml of dry DMSO and treated with 1.7 g of KF/alumina and 0.39 g of crown ether (18-C-6). The reaction mixture was heated at 100° C. for sixty hours, cooled and poured into 100 ml of water. The mixture was extracted twice with 250 ml of diethyl ether. The extracts were washed with water and then brine, combined, dried over MgSO$_4$ and concentrated. Medium-pressure liquid chromatography over silica using 30:1 hexane/ethyl acetate afforded 2.32 g (60% yield) of the subtitle compound.

B. Preparation of 4-(4-fluorophenoxy)benzyl alcohol

Lithium aluminum hydride (0.25 g, 6.69 mmol) was slurried in 20 ml of dry diethyl ether and cooled in an ice bath. The ethyl 4-(4-fluorophenoxy)benzoate (2.32 g, 8.91 mmol) in 5 ml of dry diethyl ether was added dropwise and the reaction was stirred at room temperature overnight. More lithium aluminum hydride (0.25 g) was added and the reaction was stirred for four hours. The reaction was carefully quenched by sequential addition of 0.5 ml of water, 0.5 ml of 15% NaOH solution in water, and 1.5 ml of water. The resulting white precipitate was filtered using celite and washed with diethyl ether and discarded. The filtrate and washings were combined and concentrated to afford 1.92 g (99%) of the subtitle compound.

C. Preparation of 4-(4-fluorophenoxy)benzyl bromide 4-(4-Fluorophenoxy)benzyl alcohol (1.92 g, 8.80 mmol) and 0.2 ml of pyridine was dissolved in 25 ml of benzene and cooled in cold water. Phosphorus tribromide (1.19 g, 4.40 mmol) in 10 ml of benzene was added dropwise and the reaction was stirred 30 minutes and allowed to warm to room temperature. The solvent was evaporated and the residue was carefully quenched with saturated sodium bicarbonate solution. After dilution with water, the mixture was extracted twice with diethyl ether. The organic extracts were washed with saturated sodium bicarbonate solution and then with brine, dried over MgSO$_4$, and concentrated to afford 2.38 g (96%) of the subtitle compound.

D. Preparation of 3-(2,6-dichlorophenylsulfonylamino)-4-(2-pyridyl)-5-(4-(4-fluorophenoxy)benzylthio)-(1H)-pyrazole By substantially following the procedures described for Example 1, Steps A, B, and C the compound 3-(2,6-dichlorophenylsulfonylamino)-4-(2-pyridyl)-5-(4-(4-fluorophenoxy)benzylthio)-(1H)-pyrazole was afforded. mp. 185–6° C.

Elemental analysis: Calc. C 53.91 H 3.18 N 9.31 Found C 53.85 H 3.20 N 9.12

EXAMPLE 6

Preparation of 3-(2,6-dichlorophenylsulfonylamino)-4-(2-(4-methoxy)pyridyl)-5-(4-fluorobenzylthio)-(1H)-pyrazole

A. 2-hydroxymethyl-4-methoxypyridine

The 4-methoxypyridine—N-oxide (6.3 g, 0.05 mol) was suspended in 150 ml of dichloromethane (CH$_2$Cl$_2$). Trimethyloxoniumtetrafluoroborate (7.5 g, 0.05 mol) was added all at once and the reaction was stirred at room temperature for 2 hrs. After evaporation of the solvent, the residue was dissolved in methanol (150 ml) and heated to reflux. To this solution was added of ammonium persulfate (2.3 g) in 20 ml of water. After 30 min. a further portion of 1.2 g of persulfate in 5 ml of water was added. After refluxing for one hour the solution was cooled and concentrated under vacuum. The residue was chromatographed over silica with 9:1 chloroform/methanol to give 3.52 g (51% yield) of the subtitle compound.

B. 4-methoxy-2-p-toluenesulfonyloxymethylpyridine

The 2-hydroxymethyl-4-methoxypyridine, (3.48 g, 0.024 mol) was dissolved in 50 ml $CH_2Cl_2$ and cooled to 0° C. The p-toluenesulfonyl chloride (5.7 g, 0.03 mol) was added followed by triethylamine (5 g), in 10 ml of $CH_2Cl_2$. After 15 minutes, the reaction was stirred at room temperature for one hour. The reaction was diluted with $CH_2Cl_2$ (200 ml) and washed with water. The organic layer was separated and dried with $MgSO_4$, filtered and concentrated to afford 7.3 g of crude subtitle compound suitable for further use.

C. 2-cyanomethyl-4-methoxypyridine

The 4-methoxy-2-p-toluenesulfonoxymethylpyridine (7.3 g, 0.024 mol) was added to a suspension of powdered sodium cyanide, (4.68 g, 0.096 mol) in 100 ml of dimethyl formamide. The solution turned red and was stirred 24 hrs. and then concentrated under vacuum. After dilution with water, the mixture was extracted with ethyl acetate and washed with water and then brine. The organic layer was dried over $MgSO_4$, filtered and concentrated to dryness. The residue was chromatographed over silica with 2:1 hexane/ethyl acetate to afford 0.8 g of the subtitle compound.

D. By substantially following the procedures described in Example 1 Step A, B and C the compound 3-(2,6-dichlorophenylsulfonylamino)-4-(2-(4-methoxy)pyridyl)-5-(4-fluorobenzylthio)-(1H)-pyrazole was afforded mp. 219–21° C.

Elemental analysis: Calc. C 48.98 H 3.18 N 10.39 Found C 49.04 H 3.18 N 10.59

EXAMPLE 7

Preparation of 3-(2,6-dichlorophenylsulfonylamino)-4-(2-pyridyl)-5-(4-(3-cyanopropoxy)benzylthio)-(1H)-pyrazole A. 4-(3-cyanopropyloxy)benzyl alcohol The 4-hydroxybenzyl alcohol (24.8 g, 0.2 mol) and 3-bromopropionitrile (29.6 g, 0.2 mol) were dissolved in 250 ml of 2-butanone. Potassium carbonate (30 g) and catalytic potassium iodide (0.2 g) were added and the reaction was refluxed for 48 hrs. After cooling, water was added and the layers were separated. The organic layer was washed with water, 1N sodium hydroxide and water again, dried over $MgSO_4$, filtered, and concentrated to dryness. The resultant oil was slurried in hexane and the precipitate was filtered to afford 40.5 g of the subtitle compound.

B. By substantially following the procedures described in Example 5 Step C and Example 1 Step A, B and C the compound 3-(2,6-dichlorophenylsulfonylamino)-4-(2-pyridyl)-5-(4-(3-cyanopropoxy)benzylthio)-(1H)-pyrazole was afforded mp. 198–200° C.
Elemental analysis: Calc. C 52.27 H 3.68 N 12.19 Found C 52.50 H 3.81 N 12.23

EXAMPLE 8

Preparation of 3-(2,6-dichlorophenylsulfonylamino)-4-(2-pyridyl)-5-(4-(3-carboxypropoxy)benzylthio)-(1H)-pyrazole The 3-(2,6-dichlorophenyl)sulfonylamino-4-(2-pyridyl)-5-(4-(3-cyanopropoxy)benzylthio)-(1H)-pyrazole (0.19 g), prepared as described in Example 7, above, in 2 ml of diethylene glycol and 0.2 ml of water with 0.1 g of potassium hydroxide was heated at 100° C. overnight. After cooling, the reaction was poured into a saturated solution of ammonium chloride, extracted in tetrahydrofuran/ethyl acetate 1:1, and washed with water and then brine. The organic phase was dried over $MgSO_4$, filtered and concentrated to dryness. The residue was treated with ethanol/ether 2:1 to precipitate a yellow solid (0.130 g, 66% yield) isolated by filtration.

mp. 183–5° C.

Elemental analysis: Calculated C 50.59 H 3.74 N 9.44 Found C 51.04 H 3.76 N 10.09

EXAMPLE 9

Preparation of 3-(2-methyl-5-fluorophenylsulfonylamino)-4-(2-pyridyl)-5-(4-(3-carboxyeamidopropoxy)benzylthio)-(1H)-pyrazole The 3-(2-methyl-5-fluorophenyl)sulfonylamino-4-(2-pyridyl)-5-(4-(3-cyanopropoxy)benzylthio)-(1H)-pyrazole (0.537 g), prepared as described in Example 7, above, in 10 ml of dimethyl sulfoxide was treated with 0.5 g of potassium carbonate and 2 ml of 30% hydrogen peroxide and stirred at room temperature overnight. The mixture was diluted with water and brine and extracted with ethyl acetate/tetrahydrofuran, (2:1), and washed with brine. The organic layer was dried over $MgSO_4$ and concentrated under vacuum to dryness. A solution of 10% of methanol in chloroform was added to the residue and a solid was separated by filtration. The mother liquor was subjected to chromatography over silica with 10% methanol in chloroform to give a greenish oil that crystallized from a minimum amount of methanol to afford 0.160 g (28% yield) of the desired product.

mp. 105–7° C.

Elemental analysis: Calc. C 56.20 H 4.72 N 12.60 Found C 55.93 H 4.73 N 12.51

EXAMPLE 10

Preparation of 3-(2-methyl-5-fluorophenylsulfonylamino)-4-(2-pyridyl)-5-(4-(3-tetrazolylpropoxy)benzylthio)-(1H)-pyrazole The 3-(2-methyl-5-fluorophenyl)sulfonylamino-4-(2-pyridyl)-5-(4-(3-cyanopropoxy)benzylthio)-(1H)-pyrazole (0.537 g), prepared as described in Example 7, above, in diethylene glycol was treated with 1.5 equivalents of tributyltin azide and heated at reflux temperature overnight. After cooling, 2N hydrochloric acid (2 ml) was added and the mixture was stirred 1 hr at room temperature. After extraction with tetrahydrofuran, the organic layer was washed with brine, dried over $MgSO_4$ and concentrated under vacuum. Flash chromatography over silica with 3:1 chloroform/ethyl acetate (1 1.), followed by the same solvent plus 5% methanol afforded 0.256 g (44% yield) of the pure product which crystallized from chloroform.

mp. 103° C.

Elemental analysis: Calc. C 53.78 H 4.34 N 19.30 Found C 53.55 H 4.31 N 19.46

EXAMPLE 11

Preparation of 3-(2,6-dichlorophenylsulfonylamino)-4-(2-pyridyl)-5-(4-carbamidobenzylthio)-(1H)-pyrazole 3-(2,6-Dichlorophenyl)sulfonylamino-4-(2-pyridyl)-5-(4-cyanobenzylthio)-(1H)-pyrazole (0.516 g)(prepared substantially as described in Example 1, steps A–C, above, using 19.6 g of 4-cyanobenzyl bromide in 10 ml of dimethyl sulfoxide was treated with 2 ml of 30% hydrogen peroxide and 0.5 g of potassium carbonate and stirred at room temperature overnight. The reaction was poured into brine and extracted with ethyl acetate. The organic layer was washed with brine, dried over $MgSO_4$, filtered and concentrated to dryness. The product was crystallized from cold ethyl acetate to afford 0.268 g (50% yield).

mp. 238–40° C.

Elemental analysis: Calculated C 49.44 H 3.21 N 13.10 Found C 49.68 H 3.26 N 13.08

The following tables illustrate additional Examples of compounds of formula I. Compounds were made following the procedures described in Schemes I–III above.

TABLE 1(a)

| ex. no. | $R_9$ | $R_{10}$ | $R_{11}$ | $R_{12}$ | $R_{13}$ | mp. (C.) |
|---|---|---|---|---|---|---|
| 12 | Cl | H | H | H | H | 199–200 |
| 13 | H | H | H | H | H | 177–8 |
| 14 | $NO_2$ | H | H | H | H | 247–8 |
| 15 | $CO_2CH_3$ | H | H | H | H | 165–7 |
| 16 | Cl | H | H | H | Cl | >250 |
| 17 | F | H | H | H | H | 170–1 |
| 18 | F | H | H | H | F | 205–7 |
| 19 | Cl | H | F | H | H | 195–6 |
| 20 | Cl | H | H | H | $CH_3$ | 193–4 |
| 21 | Cl | Cl | H | H | H | 237–8 |
| 22 | $CH_3$ | H | Cl | $CH_3$ | H | 197–8 |
| 23 | H | Cl | H | Cl | H | 230–5 |
| 24 | $CH_3$ | H | $CH_3$ | H | $CH_3$ | 153–5 |
| 25 | Cl | H | H | Cl | H | 255 |
| 26 | $CH_3$ | Cl | H | H | H | 187–8 |
| 27 | Cl | H | Cl | H | H | 238–9 |
| 28 | Cl | H | Cl | H | Cl | 225–7 |
| 29 | $CH_3$ | H | H | F | H | 198–200 |
| 30 | —$C_4H_4$— | | H | H | H | 223–5 |
| 31 | $CF_3$ | H | H | H | H | 178–80 |
| 32 | CN | H | H | H | H | 238–9 |
| 33 | $CH_3$ | H | H | $NO_2$ | H | 245–8 |
| 34 | H | H | F | H | H | 126–7 |

TABLE 1(b)

| Example No. | | Elemental Analysis | | | |
|---|---|---|---|---|---|
| | | C | H | N | S |
| Example 14 | Calculated | 46.03 | 3.35 | 17.89 | |
| | Found | 46.30 | 3.52 | 17.60 | |
| Example 15 | Calculated | 50.48 | 3.99 | 13.85 | |
| | Found | 50.56 | 3.97 | 13.62 | |
| Example 16 | Calculated | 43.38 | 2.91 | 13.49 | |
| | Found | 43.56 | 2.96 | 13.53 | |
| Example 17 | Calculated | 49.44 | 3.60 | 15.37 | |
| | Found | 49.59 | 3.71 | 15.53 | |
| Example 20 | Calculated | 48.66 | 3.81 | 14.19 | |
| | Found | 48.67 | 3.81 | 14.21 | |
| Example 22 | Calculated | 49.93 | 4.19 | 13.70 | |
| | Found | 50.17 | 4.24 | 13.95 | |
| Example 25 | Calculated | 43.38 | 2.91 | 13.49 | |
| | Found | 43.67 | 3.19 | 13.54 | |
| Example 31 | Calculated | 46.37 | 3.16 | 13.52 | |
| | Found | 46.64 | 3.36 | 13.29 | |
| Example 32 | Calculated | 51.74 | 3.53 | 18.85 | |
| | Found | 51.62 | 3.57 | 18.58 | |
| Example 33 | Calculated | 47.40 | 3.73 | 17.27 | |
| | Found | 47.14 | 3.72 | 17.06 | |
| Example 34 | Calculated | 49.44 | 3.60 | 15.37 | 17.60 |
| | Found | 49.30 | 3.59 | 15.53 | 17.50 |

TABLE 2(a)

| ex. no. | $R_9$ | $R_{13}$ | n | $R_{14}$ | $R_{15}$ | $R_{16}$ | $R_{17}$ | mp. (C.) |
|---|---|---|---|---|---|---|---|---|
| 35 | $CH_3$ | Cl | 1 | H | H | H | H | 211–2 |
| 36 | $CH_3$ | H | 1 | H | H | H | H | 200–1 |
| 37 | Cl | Cl | 1 | H | H | H | H | 205–6 |
| 38 | H | H | 1 | H | H | H | H | 164–5 |
| 39 | Cl | H | 1 | H | H | H | H | 213–4 |
| 40 | $CH_3$ | H | 1 | H | H | $O(CH_2)_3CN$ | H | 135–6 |
| 41 | $CH_3$ | H | 1 | H | H | H | H | 194–5 |
| 42 | Cl | Cl | 1 | H | $OCH_3$ | $OCH_3$ | H | 204–5 |
| 43 | Cl | Cl | 1 | H | $CH_3$ | $OCH_3$ | H | 203–5 |
| 44 | Cl | Cl | 1 | H | Cl | Cl | H | 211–3 |
| 45 | Cl | Cl | 1 | H | —$OCH_2O$— | | H | 211–2 |
| 46 | Cl | Cl | 1 | H | H | CN | H | 265 |
| 47 | Cl | Cl | 1 | (N) | —$C_4H_4$— | | H | 189–90 |
| 48 | Cl | Cl | 3 | H | H | $OCH_3$ | H | 179–81 |
| 49 | Cl | Cl | 1 | H | H | $O(c-C_5H_9)$ | H | 185–6 |
| 50 | Cl | Cl | 1 | H | H | $NO_2$ | H | 247–9 |
| 51 | Cl | Cl | 1 | —$OCH_2O$— | | H | F | 229–30 |
| 52 | Cl | Cl | 1 | —$C_4H_4$— | | H | H | 202–3 |
| 53 | $CH_3$ | Cl | 1 | H | H | $OCH_3$ | H | 195–8 |
| 54 | H | H | 1 | H | H | H | H | 212–3.5 |
| 55 | Cl | Cl | 1 | H | H | $OCH_3$ | H | 218–9 |
| 56 | Cl | Cl | 1 | H | $O(CH_2)_3CN$ | H | H | 134–6 |
| 57 | Cl | Cl | 1 | H | H | $CF_3$ | H | 219–20 |
| 58 | Cl | Cl | 1 | H | H | $OCH_2Ph$ | H | 203–4 |
| 59 | Cl | Cl | 2 | H | H | H | H | 199–200 |
| 60 | Cl | Cl | 1 | H | $OCH_3$ | H | H | 160–1 |
| 61 | Cl | Cl | 1 | H | H | F | H | 241–2 |
| 62 | Cl | Cl | 3 | H | H | H | H | 144–5 |
| 63 | Cl | Cl | 1 | H | H | OPh | H | 173.5–4 |
| 64 | Cl | Cl | 3* | H | H | H | H | 198–9 |
| 65 | Cl | Cl | 5 | H | H | H | H | 155–5.5 |
| 66 | Cl | Cl | 1 | H | H | $SCH_3$ | H | 215–7.5 |
| 67 | Cl | Cl | 1 | H | OPh | H | H | 150–1 |
| 68 | Cl | Cl | 1 | H | H | $CH_3$ | H | 222–3 |
| 69 | Cl | Cl | 1 | (N) | H | H | H | 185–6 |
| 70 | Cl | Cl | 1 | 4-(2-methylthiazole) | | | H | 189–90.5 |
| 71 | Cl | Cl | 1 | H | $OCH_2Ph$ | H | H | 160–1.5 |
| 72 | Cl | Cl | 1 | H | H | $CH_2Ph$ | H | 139–40 |
| 73 | Cl | Cl | 1 | $OCH_3$ | H | H | H | 195.5–7.5 |
| 74 | Cl | Cl | 1 | H | $OCH_3$ | $OCH_2Ph$ | H | 183.5–4.5 |
| 75 | Cl | Cl | 1 | H | $OPh(p-OCH_3)$ | H | H | 139.5–41 |
| 76 | Cl | Cl | 1 | H | H | $OCH_2Ph(p-F)$ | H | 214–5 |
| 77 | Cl | Cl | 3# | H | H | H | H | 184–5 |
| 78 | Cl | Cl | 1 | H | OPh(o-F) | H | H | 186–7 |
| 79 | Cl | Cl | 1 | H | H | $O-3-(c-C_6H_9)$ | H | 174–5 |
| 80 | Cl | Cl | 2 | H | H | $OCH_2Ph$ | H | 179–81 |
| 81 | Cl | Cl | 1 | H | H | SPh(p-F) | H | 173–5 |
| 82 | Cl | Cl | 1 | F | H | H | H | 215–6 |
| 83 | Cl | Cl | 1 | $CH_3$ | H | H | H | 168–9 |
| 84 | Cl | Cl | 1 | Cl | H | H | H | 201–2 |
| 85 | Cl | Cl | 1 | $OCH_2Ph$ | H | H | H | 192–3 |
| 86 | Cl | Cl | 1 | OPh | H | H | H | 168–9 |
| 87 | Cl | Cl | 1 | $CH_2Ph$ | H | H | H | 176–8 |
| 88 | $CH_3$ | $CH_3$ | 1 | H | $OCH_2Ph$ | H | H | 133–6 |
| 89 | Cl | Cl | 1 | H | H | Ph | H | 206–8 |
| 90 | Cl | Cl | 1 | Ph | H | H | H | 155–8 |
| 91 | Cl | Cl | 1 | H | Ph | H | H | 167–8 |

\* = —$CH_2CH=CH$— (E)
\# = —$CH_2CH_2O$—
$R^{10}$ is hydrogen except for Example No. 36 where $R^{10}$ is chlorine.
$R^{11}$ is hydrogen except for Example No. 54 where $R^{11}$ is chlorine.
$R^{12}$ is hydrogen except for Example Nos. 40 and 41 where $R^{12}$ is fluorine.

TABLE 2(b)

Elemental Analysis

| Example No. | | C | H | N | S | Cl |
|---|---|---|---|---|---|---|
| Example 36 | | | | | | |
| | Calculated | 56.10 | 4.07 | 11.90 | | |
| | Found | 56.30 | 4.18 | 12.00 | | |
| Example 37 | | | | | | |
| | Calculated | 51.33 | 3.28 | 11.40 | | |
| | Found | 51.50 | 3.33 | 11.33 | | |
| Example 39 | | | | | | |
| | Calculated | 55.20 | 3.75 | 12.26 | | |
| | Found | 54.99 | 3.83 | 12.51 | | |
| Example 40 | | | | | | |
| | Calculated | 58.09 | 4.50 | 13.03 | | |
| | Found | 58.20 | 4.54 | 12.81 | | |
| Example 41 | | | | | | |
| | Calculated | 58.13 | 4.21 | 12.33 | | |
| | Found | 58.43 | 4.31 | 12.63 | | |
| Example 42 | | | | | | |
| | Calculated | 50.09 | 3.66 | 10.16 | | |
| | Found | 49.91 | 3.67 | 10.05 | | |
| Example 46 | | | | | | |
| | Calculated | 51.17 | 2.93 | 13.56 | | |
| | Found | 51.44 | 3.03 | 13.40 | | |
| Example 48 | | | | | | |
| | Calculated | 52.46 | 4.04 | 10.20 | | |
| | Found | 52.35 | 4.17 | 10.29 | | |
| Example 50 | | | | | | |
| | Calculated | 47.02 | 2.82 | 13.06 | | |
| | Found | 47.28 | 2.97 | 12.97 | | |
| Example 51 | | | | | | |
| | Calculated | 48.68 | 3.02 | 9.87 | | |
| | Found | 48.89 | 3.20 | 9.90 | | |
| Example 53 | | | | | | |
| | Calculated | 55.14 | 4.22 | 11.18 | 12.80 | 7.08 |
| | Found | 55.00 | 4.18 | 10.99 | 13.03 | 7.30 |
| Example 54 | | | | | | |
| | Calculated | 55.20 | 3.75 | 12.26 | | |
| | Found | 55.28 | 3.84 | 12.25 | | |
| Example 55 | | | | | | |
| | Calculated | 50.68 | 3.48 | 10.74 | 12.30 | 13.60 |
| | Found | 50.75 | 3.53 | 10.70 | 12.21 | 13.32 |
| Example 56 | | | | | | |
| | Calculated | 52.27 | 3.68 | 12.19 | | |
| | Found | 52.23 | 3.66 | 12.10 | | |
| Example 57 | | | | | | |
| | Calculated | 47.24 | 2.70 | 10.02 | 11.46 | 12.67 |
| | Found | 47.21 | 2.75 | 10.09 | 11.26 | 12.38 |
| Example 58 | | | | | | |
| | Calculated | 56.28 | 3.71 | 9.38 | 10.73 | 11.87 |
| | Found | 56.04 | 3.81 | 9.29 | 10.50 | 12.11 |
| Example 59 | | | | | | |
| | Calculated | 52.28 | 3.59 | 11.08 | 12.69 | 14.02 |
| | Found | 52.33 | 3.63 | 11.05 | 12.44 | 13.91 |
| Example 60 | | | | | | |
| | Calculated | 50.68 | 3.48 | 10.74 | 12.30 | 13.60 |
| | Found | 50.71 | 3.64 | 10.44 | 12.45 | 13.36 |
| Example 62 | | | | | | |
| | Calculated | 53.18 | 3.88 | 10.79 | 12.34 | 13.65 |
| | Found | 53.34 | 4.07 | 10.51 | 12.13 | 13.53 |
| Example 63 | | | | | | |
| | Calculated | 55.58 | 3.46 | 9.60 | 10.99 | 12.15 |
| | Found | 55.84 | 3.67 | 9.56 | 10.78 | 11.92 |
| Example 64 | | | | | | |
| | Calculated | 53.39 | 3.51 | 10.83 | 12.39 | 13.70 |
| | Found | 53.52 | 3.39 | 10.88 | 12.28 | 13.98 |
| Example 65 | | | | | | |
| | Calculated | 54.84 | 4.42 | 10.23 | 11.71 | 12.95 |
| | Found | 55.10 | 4.43 | 10.27 | 11.47 | 12.85 |
| Example 67 | | | | | | |
| | Calculated | 55.58 | 3.46 | 9.60 | 10.99 | 12.15 |
| | Found | 55.84 | 3.54 | 9.45 | 10.94 | 12.41 |
| Example 68 | | | | | | |
| | Calculated | 52.28 | 3.59 | 11.09 | | |
| | Found | 52.32 | 3.54 | 10.88 | | |

TABLE 2(b)-continued

Elemental Analysis

| Example No. | | C | H | N | S | Cl |
|---|---|---|---|---|---|---|
| Example 70 | | | | | | |
| | Calculated | 44.53 | 2.95 | 13.67 | 18.77 | 13.84 |
| | Found | 44.56 | 2.91 | 13.69 | 18.50 | 13.82 |
| Example 71 | | | | | | |
| | Calculated | 56.28 | 3.71 | 9.38 | 10.73 | 11.87 |
| | Found | 56.51 | 3.77 | 9.52 | 10.55 | 11.82 |
| Example 72 | | | | | | |
| | Calculated | 57.83 | 3.81 | 9.63 | 11.03 | 12.19 |
| | Found | 58.12 | 3.81 | 9.64 | 10.47 | 12.14 |
| Example 73 | | | | | | |
| | Calculated | 50.68 | 3.48 | 10.74 | 12.30 | 13.60 |
| | Found | 50.89 | 3.71 | 10.64 | | |
| Example 75 | | | | | | |
| | Calculated | 54.81 | 3.61 | 9.13 | 10.45 | 11.56 |
| | Found | 54.99 | 3.60 | 9.21 | 10.17 | 11.33 |
| Example 76 | | | | | | |
| | Calculated | 54.64 | 3.44 | 9.10 | | |
| | Found | 54.80 | 3.58 | 8.99 | | |
| Example 77 | | | | | | |
| | Calculated | 50.67 | 3.48 | 10.74 | 12.30 | |
| | Found | 50.68 | 3.52 | 10.73 | 11.94 | |
| Example 78 | | | | | | |
| | Calculated | 53.91 | 3.18 | 9.31 | | |
| | Found | 54.20 | 3.16 | 9.47 | | |
| Example 79 | | | | | | |
| | Calculated | 55.20 | 4.12 | 9.54 | | |
| | Found | 54.89 | 3.92 | 9.70 | | |
| Example 80 | | | | | | |
| | Calculated | 56.95 | 3.96 | 9.16 | 10.48 | 11.59 |
| | Found | 57.16 | 4.03 | 9.21 | 10.46 | 11.72 |
| Example 81 | | | | | | |
| | Calculated | 52.51 | 3.10 | 9.07 | 15.58 | 11.48 |
| | Found | 52.74 | 3.28 | 9.22 | 15.24 | 11.48 |
| Example 82 | | | | | | |
| | Calculated | 49.52 | 2.97 | 10.99 | 12.59 | 13.92 |
| | Found | 49.29 | 3.17 | 10.78 | 12.35 | 14.17 |
| Example 83 | | | | | | |
| | Calculated | 52.28 | 3.59 | 11.09 | 12.69 | 14.03 |
| | Found | 52.27 | 3.63 | 10.95 | 12.42 | 13.96 |
| Example 84 | | | | | | |
| | Calculated | 47.96 | 2.87 | 10.65 | 12.19 | 20.23 |
| | Found | 48.25 | 2.96 | 10.67 | 11.98 | 19.96 |
| Example 85 | | | | | | |
| | Calculated | 56.28 | 3.71 | 9.38 | 10.73 | 11.87 |
| | Found | 56.31 | 3.90 | 9.47 | 10.17 | 11.51 |
| Example 86 | | | | | | |
| | Calculated | 55.58 | 3.46 | 9.60 | 10.99 | 12.15 |
| | Found | 55.75 | 3.63 | 9.77 | 10.99 | 12.22 |
| Example 87 | | | | | | |
| | Calculated | 57.83 | 3.81 | 9.63 | 11.03 | 12.19 |
| | Found | 58.12 | 3.92 | 9.73 | 10.85 | 12.43 |
| Example 89 | | | | | | |
| | Calculated | 57.14 | 3.55 | 9.87 | | |
| | Found | 57.26 | 3.74 | 9.97 | | |
| Example 90 | | | | | | |
| | Calculated | 57.14 | 3.55 | 9.87 | | |
| | Found | 56.88 | 3.55 | 9.73 | | |
| Example 91 | | | | | | |
| | Calculated | 57.14 | 3.55 | 9.87 | | |
| | Found | 57.33 | 3.64 | 10.13 | | |

TABLE 3(a)

[Structure: pyrazole core with R17, R16, R15, R14 on benzyl ring via (CH2)n-S linkage; R18 on pyridine; R9-R13 on sulfonyl phenyl ring; NH-SO2 linkage]

| ex. no. | $R_9$ | $R_{12}$ | $R_{13}$ | n | $R_{14}$ | $R_{15}$ | $R_{16}$ | $R_{18}$ | mp. (°C) |
|---|---|---|---|---|---|---|---|---|---|
| 92 | Cl | H | Cl | * | — | — | — | $(CH_2)_2CONH_2$ | 180–2 |
| 93 | Cl | H | Cl | 1 | H | H | H | CN | 158–60 |
| 94 | Cl | H | Cl | 1 | H | H | H | $CH_2CONH_2$ | 236–9 |
| 95 | Cl | H | Cl | 1 | $CH_3$ | H | H | $CH_2CH_3$ | 172–3 |
| 96 | Cl | H | Cl | 1 | H | H | H | $(CH_2)_2CONH_2$ | 191–2 |
| 97 | Cl | H | Cl | 1 | $CH_3$ | H | H | $CH(CH_3)_2$ | 158–60 |
| 98 | Cl | H | Cl | * | — | — | — | $CH_2CONH_2$ | 246–8 |
| 99 | Cl | H | Cl | 1 | H | OPh(p-F) | H | $CH_2CONH_2$ | 242–3 |
| 100 | Cl | H | Cl | 1 | OPh | H | H | $CH_2CONH_2$ | 232.5–4 |
| 101 | Cl | H | Cl | 1 | H | H | OPh | $CH_2CONH_2$ | 232–4 |
| 102 | Cl | H | Cl | 3 | H | H | H | $CH_2CONH_2$ | 216–8 |
| 103 | Cl | H | Cl | 1 | H | H | OPh(p-F) | $CH_2CONH_2$ | 250–1 |
| 104 | $CH_3$ | F | H | 1 | H | OPh(p-F) | H | $CH_2CONH_2$ | 194–5.5 |
| 105 | $CH_3$ | H | H | 1 | H | OPh(p-F) | H | $CH_2CONH_2$ | 203–5 |

* = $CH_3$ in place of $(CH_2)_nAr$
$R^{10}$ is hydrogen except for Example No. 105 where $R^{10}$ is chlorine.

TABLE 3(b)

Elemental Analysis

| Example No. | | C | H | N | S | Cl |
|---|---|---|---|---|---|---|
| Example 93 | Calculated | 51.17 | 2.93 | 13.56 | | |
| | Found | 51.09 | 2.95 | 13.44 | | |
| Example 95 | Calculated | 54.03 | 4.16 | 10.50 | 12.02 | 13.29 |
| | Found | 54.24 | 4.17 | 10.46 | 11.82 | 13.13 |
| Example 97 | Calculated | 54.84 | 4.42 | 10.23 | 11.71 | 12.95 |
| | Found | 55.14 | 4.54 | 10.04 | 11.42 | 13.13 |
| Example 104 | Calculated | 57.96 | 4.05 | 11.26 | | |
| | Found | 58.18 | 4.03 | 11.22 | | |
| Example 105 | Calculated | 56.47 | 3.95 | 10.97 | | |
| | Found | 56.73 | 4.00 | 10.97 | | |

TABLE 4(a)

[Structure: pyrazole with R16-phenyl-(CH2)n-X- substituent, Ar group, and N-SO2-(2,6-dichlorophenyl) group, with R14]

| ex. no. | Ar | X | n | R14 | R16 | mp. (C.) |
|---|---|---|---|---|---|---|
| 106 | phenyl | S | 1 | H | OCH3 | 219–20 |
| 107 | pyrazine | S | 1 | H | H | 221–3 |
| 108 | 3-isoquinoline | S | 1 | CH3 | H | 198 |

TABLE 4(b)

Elemental Analysis

| Example No. | | C | H | N | S | Cl |
|---|---|---|---|---|---|---|
| Example 107 | | | | | | |
| | Calculated | 48.78 | 3.07 | 14.22 | | |
| | Found | 49.08 | 3.22 | 14.08 | | |
| Example 108 | | | | | | |
| | Calculated | 56.22 | 3.63 | 10.09 | | |
| | Found | 56.35 | 3.89 | 10.16 | | |

TABLE 5

[Structure: pyrazole with 2-pyridyl, SMe, and N-SO2-thiophene (R19, R20, R21) substituents]

| Ex. No. | R17 | R16 | R15 | mp. (C.) |
|---|---|---|---|---|
| 109 | Cl | Cl | H | 218–20 |
| 110 | H | H | H | 215–220 |
| 111 | Br | H | Br | 179–80 |
| 112 | Cl | H | Br | 190–3 |
| 113 | * | — | — | 248–9 |

*= 4-(3-bromo-2,5-dichlorothiophene)

TABLE 5(b)

Elemental Analysis

| Example No. | | C | H | N | S | Cl |
|---|---|---|---|---|---|---|
| Example 109 | | | | | | |
| | Calculated | 37.0 | 2.39 | 13.35 | | |
| | Found | 37.1 | 2.39 | 13.09 | | |

Therapeutic Use of Pyrazoles

The pyrazoles described herein are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenase, cyclooxygenases, and etc.

The method of the invention for inhibiting sPLA$_2$ mediated release of fatty acids comprises contacting sPLA$_2$ with an therapeutically effective amount of the compound of Formula (I), its salt or a prodrug derivative thereof.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administering to the mammal a compound of formula (I) in a therapeutically effective amount. A "therapeutically effective" amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Pharmaceutical Formulations of the Invention

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

Pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the pyrazole compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
|---|---|
| 3-(naphthylsulfonylamino)-4-(4-propoxypyridin-2-yl)-5-(5-((2-methyl-5-cyanophenyl)pent-1-yl)thio-(1H)-pyrazole | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| 3-(3-nitro-5-ethyl)phenylsulfonylamino-4-(phenyl)-5-((3-cyanoprop-1-yloxy)benzyl)thio-(1H)-pyrazole | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| 3-(2-methylphenyl)sulfonylamino-4-(isoquinolin-3-yl)-5-(4-ethyoxybenzyl)thio-(2H)-pyrazole | 0.25 |
| Ethanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
| --- | --- |
| 3-(5-bromo)phenylsulfonylamino-4-(4-ethoxypyridin-2-yl)-5-(5-phenylhepten-1-yl)thio-(1H)-pyrazole | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
| --- | --- |
| 3-(3-methoxycarbonylphenyl)sulfonylamino-4-(4-ethylcarboxamidopyridin-2-yl)-5-(2-fluorophenylthiobenzyl)thio-(2H)-pyrazole | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
| --- | --- |
| 3-(5-chlorophenyl)sulfonylamino-4-(4-ethylcarboxamidopyridin-2-yl)-5-(3-carboxyethyoxybenzyl)thio-(2H)-pyrazole | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
| --- | --- |
| 3-(5-bromophenyl)sulfonylamino-4-(4-methoxypyridin-2-yl)-5-(2-(3-cyanoprop-1-yloxy)benzyl)thio-(1H)-pyrazole | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
| --- | --- |
| 3-(4-chlorophenyl)sulfonylamino-4-(4-ethylpyridin-2-yl)-5-(2-cyano-5-ethylthiobenzyl)thio-(1H)-pyrazole | 100 mg |
| Isotonic saline | 1,000 ml |

The solution of the above ingredients generally is administered intravenously to a subject at a rate of 1 ml per minute.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader" , by Laure J. Reynolds, Lori L. Hughes, and Edward A Dennis, *Analytical Biochemistry*, 204, pp. 190–197, 1992 (the disclosure of which is incorporated herein by reference):

Reagents:
REACTION BUFFER -

CaCl$_2$.2H$_2$O (1.47 g/L)
KCl (7.455 g/L)
Bovine Serum Albumin (fatty acid free) (1 g/L)
(Sigma A-7030, product of Sigma Chemical Co.
St. Louis MO, USA)
TRIS HCl (3.94 g/L)
pH 7.5 (adjust with NaOH)
ENZYME BUFFER -

0.05 NaOAc.3H$_2$O, pH 4.5
0.2 NaCl
Adjust pH to 4.5 with acetic acid
DTNB - 5,5'-dithiobis-2-nitrobenzoic acid
RACEMIC DIHEPTANOYL THIO - PC racemic 1,2-bis(heptanoylthio)-1,2-dideoxy-sn-
glycero-3-phosphorylcholine
TRITON X-100™ prepare at 6.249 mg/ml in
reaction buffer to equal 10 uM.
TRITON X-100™ is a polyoxy ethylene non-ionic
detergent supplied by
Pierce Chemical Company,
3747 N. Meridian Road, Rockford, Illinois
61101.

Reaction Mixture

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure

1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

Compounds of the instant invention were tested in Assay Example 1 and were found to be effective at concentrations of less than 100 $\mu$M.

Assay Example 2

Method

Male Hartley strain guinea pigs (500–700 g) were killed by cervical dislocation and their heart and lungs removed intact and placed in aerated (95% O$_2$:5% CO$_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Md., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; CaCl$_2$.2H$_2$O, 2.5; MgSO$_4$.7H$_2$O, 1.2; NaHCO$_3$, 24.8; KH$_2$PO$_4$, 1.0; and dextrose, 10.0. Pleural strips from the opposite lobes of the lung were used for paired experiments. Preliminary data generated from tension/response curves demonstrated that resting tension of 800mg was optimal. The tissues were allowed to equilibrate for 45 min. as the bath fluid was changed periodically.

Cumulative Concentration-response Curves

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration (sPLA$_2$) in the tissue bath by half-log$_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of sPLA$_2$, the compounds and their respective vehicles were added to the tissues 30 minutes prior to starting the sPLA$_2$ concentration-response curves.

Statistical Analysis

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the ED$_{50}$ for the control curve, the steepness of the curves, and the pA$_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent K$_B$, the dissociation constant of the inhibitor.

To estimate the drug-induced suppression of the maximal responses, sPLA$_2$ responses (10 ug/ml) were determined in the absence and presence of drug, and percent suppression was calculated for each pair of tissues. Representative examples of inhibitory activities are presented in Table 2, below.

Ref. 1—van, J. M.: Cumulative dose-response curves. II. Technique for the making of dose-response curves in isolated organs and the evaluation of drug parameters. *Arch. Int. Pharmacodvn. Ther.,* 143: 299–330, 1963.

Ref. 2—Waud, D.: Analysis of dose-response relationships. in *Advances in General and Cellular Pharmacology* eds Narahashi, Bianchi 1:145–178, 1976.

Compounds of the instant invention were tested in Assay Example 2 and were found to be effective at concentrations below 20 μM.

While the present invention has been illustrated above by certain specific embodiments, it is not intended that these specific examples should limit the scope of the invention as described in the appended claims.

We claim:

1. A compound of the formula (I)

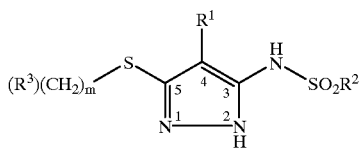

wherein:
$R^1$ is phenyl, isoquinolin-3-yl, pyrazinyl, pyridin-2-yl, pyridin-2-yl substituted at the 4-position with —$(C_1$–$C_4)$alkyl, $(C_1$–$C_4)$alkoxyl, —CN or —$(CH_2)_n$CONH$_2$ where n is 0–2;

$R^2$ is phenyl; phenyl substituted with 1 to 3 substituents selected from the group consisting of —$(C_1$–$C_4)$alkyl, —CN, halo, —NO$_2$, CO$_2(C_1$–$C_4)$alkyl and —CF$_3$; naphthyl; thiophene or thiophene substituted with 1 to 3 halo groups;

$R^3$ is hydrogen; phenyl; phenyl($C_2$–$C_6$)alkenyl; pyridyl; naphthyl; quinolinyl; $(C_1$–$C_4)$alkylthiazolyl; phenyl substituted with 1 to 2 substituents selected from the group consisting of —$(C_1$–$C_4)$alkyl, —CN, —CONH$_2$, —NO$_2$, —CF$_3$, halo, $(C_1$–$C_4)$alkoxy, CO$_2(C_1$–$C_4)$alkyl, phenoxy and SR$^4$ where R$^4$ is —$(C_1$–$C_4)$alkyl or halophenyl; phenyl substituted with one substituent selected from the group consisting of
—O(CH$_2)_p$R$^5$ where p is 1 to 3 and R$^5$ is —CN, —CO$_2$H, —CONH$_2$, or tetrazolyl,
phenyl and
—OR$^6$ where R$^6$ is cyclopentyl, cyclohexenyl, or phenyl substituted with halo or $(C_1$–$C_4)$alkoxy; or phenyl substituted with two substituents which, when taken together with the phenyl ring to which they are attached form a methylenedioxy ring; and
m is 1 to 5;
or a pharmaceutically acceptable salt, solvate, tautomer, or prodrug derivative thereof.

2. A compound of claim 1 wherein:
$R^1$ is pyridine-2-yl or pyridine-2-yl substituted at the 4-position with —$(C_1$–$C_4)$alkyl, $(C_1$–$C_4)$alkoxy, —CN or —$(CH_2)_n$CONH$_2$ where n is 0–2;
$R^2$ is phenyl substituted with 1 to 3 substituents selected from the group consisting of —$(C_1$–$C_4)$alkyl, —CN, halo, —NO$_2$, CO$_2(C_1$–$C_4)$alkyl and —CF$_3$; and
$R^3$ is phenyl; phenyl($C_2$–$C_6$)alkenyl; phenyl substituted with 1 or 2 substituents selected from the group consisting of —$(C_1$–$C_4)$alkyl, —CN, —CONH$_2$, —NO$_2$, —CF$_3$, halo, $(C_1$–$C_4)$alkoxy, CO$_2(C_1$–$C_4)$alkyl, phenoxy and SR$_4$ where R$^4$ is —$(C_1$–$C_4)$alkyl or halo phenyl;
phenyl substituted with one substituent selected from the group consisting of —O(CH$_2)_p$R$^5$ where p is 1 to 3 and R$^5$ is —CN, —CO$_2$H, —CONH$_2$ or tetrazolyl, phenyl and —OR$^6$ where R$^6$ is cyclopentyl, cyclohexenyl or phenyl substituted with halo or $(C_1$–$C_4)$alkoxy;
or phenyl substituted with two substituents which when taken together with the phenyl ring to which they are attached form a methylenedioxy ring.

3. A compound of claim 2 wherein:
$R^1$ is pyridin-2-yl substituted at the 4-position with $(CH_2)_n$CONH$_2$ where n is 1; and
$R^2$ is phenyl substituted with one or two substituents selected from the group consisting of —$(C_1$–$C_4)$alkyl or halo.

4. A compound of claim 1 selected from the group consisting of 3-(2-chloro-6-methylphenylsulfonylamino)-4-(2-(4-acetamido)pyridyl)-5-(3-(4-fluorophenoxy)benzylthio)-(1H)-pyrazole and 3-(2,6-dichlorophenylsulfonylamino)-4-(2-(4-acetamido)pyridyl)-5-(3-(4-fluorophenoxy)benzylthio)-(1H)-pyrazole or a pharmaceutically acceptable salt, solvate, tautomer, or prodrug derivative thereof.

5. A pharmaceutical formulation comprising a compound as claimed in claim 1 together with a pharmaceutically acceptable carrier or diluent therefor.

6. A method for selectively inhibiting sPLA2 in alleviating the pathological effects of septic shock, adult respiratory distress syndrome, pancreatitis, trauma-induced shock, bronchial asthma, allergic rhinitis, and rheumatoid arthritis which comprises administering to a mammal in need of such treatment a compound of formula I in claim 1 in an amount sufficient to inhibit sPLA$_2$ mediated release of fatty acid and to thereby inhibit or prevent the arachidonic acid cascade and its deleterious products.

7. A process for preparing a compound of formula I in claim 1:

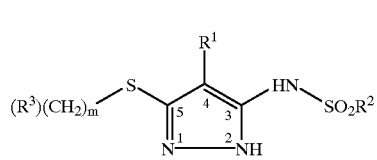

wherein:
$R^1$ is phenyl, isoquinolin-3-yl, pyrazinyl, pyridin-2-yl, pyridin-2-yl substituted at the 4-position with —$(C_1$–$C_4)$alkyl, $(C_1$–$C_4)$alkoxyl, —CN or —$(CH_2)_n$CONH$_2$ where n is 0–2;
$R^2$ is phenyl; phenyl substituted with 1 to 3 substituents selected from the group consisting of —$(C_1$–$C_4)$alkyl, —CN, halo, —NO$_2$, CO$_2(C_1$–$C_4)$alkyl and —CF$_3$; naphthyl; thiophene or thiophene substituted with 1 to 3 halo groups;
$R^3$ is hydrogen; phenyl; phenyl($C_2$–$C_6$)alkenyl; pyridyl; naphthyl; quinolinyl; $(C_1$–$C_4)$alkylthiazolyl; phenyl substituted with 1 to 2 substituents selected from the group consisting of —$(C_1$–$C_4)$alkyl, —CN, —CONH$_2$, —NO$_2$, —CF$_3$, halo, $(C_1$–$C_4)$alkoxy, CO$_2(C_1$–$C_4)$alkyl, phenoxy and SR$^4$ where R$^4$ is —$(C_1$–$C_4)$alkyl or halophenyl; phenyl substituted with one substituent selected from the group consisting of —O(CH$_2$)$_p$R$^5$ where p is 1 to 3 and R$^5$ is —CN, —CO$_2$H, —CONH$_2$, or tetrazolyl, phenyl and —OR$^6$ where R$^6$ is cyclopentyl, cyclohexenyl, or phenyl substituted with halo or (C$_1$–C$_4$)alkoxy; or phenyl substituted with two substituents which, when taken together with the phenyl ring to which they are attached form a methylenedioxy ring; and m is 1 to 5;

or a pharmaceutically acceptable salt, solvate, tautomer, or prodrug derivative thereof;

which comprises reacting a compound of formula III

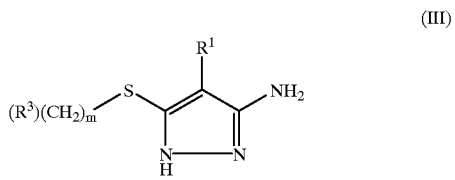

(III)

where R$^3$, R$^1$ and m are as defined above with a compound of formula

R$^2$SO$_2$Cl    (II)

where R$^2$ is as defined above.

8. A process of claim 7 wherein

R$^1$ is pyridine-2-yl or pyridine-2-yl substituted at the 4-position with —(C$_1$–C$_4$)alkyl, (C$_1$–C$_4$)alkoxy, —CN or —(CH$_2$)$_n$CONH$_2$ where n is 0–2;

R$^2$ is phenyl substituted with 1 to 3 substituents selected from the group consisting of —(C$_1$–C$_4$)alkyl, —CN, halo, —NO$_2$, CO$_2$(C$_1$–C$_4$)alkyl and —CF$_3$; and R$^3$ is phenyl; phenyl(C$_2$–C$_6$)alkenyl; phenyl substituted with 1 or 2 substituents selected from the group consisting of —(C$_1$–C$_4$)alkyl, —CN, —CONH$_2$, —NO$_2$, —CF$_3$, halo, (C$_1$–C$_4$)alkoxy, CO$_2$(C$_1$–C$_4$)alkyl, phenoxy and SR$_4$ where R$^4$ is —(C$_1$–C$_4$)alkyl or halo phenyl;

phenyl substituted with one substituent selected from the group consisting of —O(CH$_2$)pR$^5$ where p is 1 to 3 and R$^5$ is —CN, —CO$_2$H, —CONH$_2$ or tetrazolyl, phenyl and —OR$^6$ where R$^6$ is cyclopentyl, cyclohexenyl or phenyl substituted with halo or (C$_1$–C$_4$)alkoxy;

or phenyl substituted with two substituents which when taken together with the phenyl ring to which they are attached form a methylenedioxy ring.

9. A process of claim 8 wherein

R$^1$ is pyridin-2-yl substituted at the 4-position with (CH$_2$)$_n$ CONH$_2$ where n is 1; and R$^2$ is phenyl substituted with one or two substituents selected from the group consisting of —(C$_1$–C$_4$)alkyl or halo.

10. A process of claim 9 which prepares a compound of claim 1 selected from the group consisting of 3-(2-chloro-6-methylphenylsulfonylamino)-4-(2-(4-acetamido)pyridyl)-5-(3-(4-fluorophenoxy)benzylthio)-(1H)-pyrazole and 3-(2,6-dichlorophenylsulfonylamino)-4-(2-(4-acetamido)pyridyl)-5-(3-(4-fluorophenoxy)benzylthio)-(1H)-pyrazole.

* * * * *